(12) United States Patent
Luttrell

(10) Patent No.: US 10,506,950 B2
(45) Date of Patent: Dec. 17, 2019

(54) RESPIRATORY THERAPY INSTRUMENT OFFERING GAME-BASED INCENTIVES, TRAINING, AND TELEMETRY COLLECTION

(71) Applicant: COMPLIANT GAMES, INC., Memphis, TN (US)

(72) Inventor: Robert Shane Luttrell, Memphis, TN (US)

(73) Assignee: Compliant Games, Inc., Memphis, TN (US)

( * ) Notice: Subject to any disclaimer, the term of this patent is extended or adjusted under 35 U.S.C. 154(b) by 582 days.

(21) Appl. No.: 15/086,014

(22) Filed: Mar. 30, 2016

(65) Prior Publication Data

US 2016/0287139 A1   Oct. 6, 2016

Related U.S. Application Data

(60) Provisional application No. 62/141,623, filed on Apr. 1, 2015.

(51) Int. Cl.
*A61B 5/087*   (2006.01)
*A61B 5/00*   (2006.01)
(Continued)

(52) U.S. Cl.
CPC ............... *A61B 5/087* (2013.01); *A61B 5/11* (2013.01); *A61B 5/4833* (2013.01);
(Continued)

(58) Field of Classification Search
CPC . A61B 5/087; A61B 5/486; A61B 2562/0247; A61B 2560/0475;
(Continued)

(56) References Cited

U.S. PATENT DOCUMENTS

| | | | |
|---|---|---|---|
| 6,176,833 B1 * | 1/2001 | Thomson | A61B 5/087 600/538 |
| 6,203,502 B1 | 3/2001 | Hilgendorf et al. | |

(Continued)

FOREIGN PATENT DOCUMENTS

| | | |
|---|---|---|
| CN | 101318075 B | 10/2010 |
| WO | 2016161036 A1 | 10/2016 |

OTHER PUBLICATIONS

"International Preliminary Report on Patentability" (ISA/US) in Compliant Games, Inc., International Patent Application Serial No. PCT/US2016/025093, dated Oct. 3, 2017 (6 pages).

(Continued)

*Primary Examiner* — Tiffany Weston
(74) *Attorney, Agent, or Firm* — Tillman Wright, PLLC; David R. Higgins; Neal B. Wolgin

(57) ABSTRACT

A respiratory therapy instrument providing a telehealth platform for pulmonary care includes a housing with opposed extension arms, an airway tube removably clamped between the opposed extension arms, a pair of pressure sensors, and a circuit board retained within the housing. The pressure sensors are in communication with an interior of the airway tube and are configured to detect pulmonary flow data within the airway tube. The circuit board is configured to collect the pulmonary flow data detected by the pair of pressure sensors and includes a transmitter to send data, including the collected pulmonary flow data, wirelessly to a computing device. The collected pulmonary flow data is utilized in game play for an incentivization game operated on the computing device. The respiratory therapy instrument is configurable for use in a first configuration, whereby the respiratory therapy instrument operates to adapt an existing respiratory therapy device for telehealth functionality, or in a second configuration, whereby the respiratory therapy (Continued)

instrument operates as an independent respiratory therapy device with telehealth functionality.

14 Claims, 18 Drawing Sheets

(51) Int. Cl.
| | |
|---|---|
| *G07F 17/32* | (2006.01) |
| *A61B 5/11* | (2006.01) |
| *A61M 16/00* | (2006.01) |
| *A61M 16/08* | (2006.01) |
| *A61M 11/00* | (2006.01) |
| *A61M 15/00* | (2006.01) |
| *A61M 16/20* | (2006.01) |

(52) U.S. Cl.
CPC .......... *A61B 5/4836* (2013.01); *A61B 5/4848* (2013.01); *A61M 16/0006* (2014.02); *A61M 16/0051* (2013.01); *A61M 16/021* (2017.08); *A61M 16/0858* (2014.02); *G07F 17/3244* (2013.01); *A61B 5/0022* (2013.01); *A61B 2560/0425* (2013.01); *A61B 2562/0247* (2013.01); *A61M 11/00* (2013.01); *A61M 15/00* (2013.01); *A61M 16/201* (2014.02); *A61M 2016/0027* (2013.01); *A61M 2016/0036* (2013.01); *A61M 2205/3553* (2013.01); *A61M 2205/3584* (2013.01); *A61M 2205/3592* (2013.01); *A61M 2206/20* (2013.01)

(58) Field of Classification Search
CPC . A61B 5/0022; A61B 2560/0425; A61B 5/11; A61B 5/4836; A61B 5/1118; A61B 5/4833; A61B 5/4848; G07F 17/3244; A63F 9/00; A61M 16/00; A61M 2016/0036; A61M 2205/3584; A61M 16/201; A61M 2205/3553; A61M 2205/3592; A61M 2016/0027; A61M 11/00; A61M 2206/20; A61M 15/00; A61M 16/0051; A61M 16/0006; A61M 16/0858

See application file for complete search history.

(56) References Cited

U.S. PATENT DOCUMENTS

| | | |
|---|---|---|
| D557,788 S | 12/2007 | Eloranta |
| 7,625,345 B2 | 12/2009 | Quinn |
| 8,689,561 B2 | 4/2014 | Lin |
| 2011/0092840 A1* | 4/2011 | Forbes .................. A61B 5/0876 600/538 |
| 2013/0066225 A1* | 3/2013 | Kojouri .................. A61B 5/087 600/538 |
| 2013/0184540 A1 | 7/2013 | Boschetti Sacco et al. |
| 2013/0303930 A1 | 11/2013 | Elefteriades et al. |
| 2014/0100470 A1 | 4/2014 | Perry |
| 2015/0258370 A1* | 9/2015 | Arkush .................. A61B 5/087 482/8 |

OTHER PUBLICATIONS

Heinrich, Aaron, "Wing lung monitor aimed at letting asthmatics breathe easier," Gizmag, available at http://www.gizmag.com/winglets-you-measure-your-lungs-via-your-smartphone/40046/, accessed as of Apr. 22, 2016 (5 pages).

Welch Allyn, "Welch Allyn PC-Based SpiroPerfect Spirometer," SM2863 Rev C, 2011 (4 pages).

"International Search Report" and "Written Opinion of the International Searching Authority" (ISA/US) in Compliant Games, Inc., International Patent Application Serial No. PCT/US2016/025093, dated Jul. 22, 2016 (8 pages).

* cited by examiner

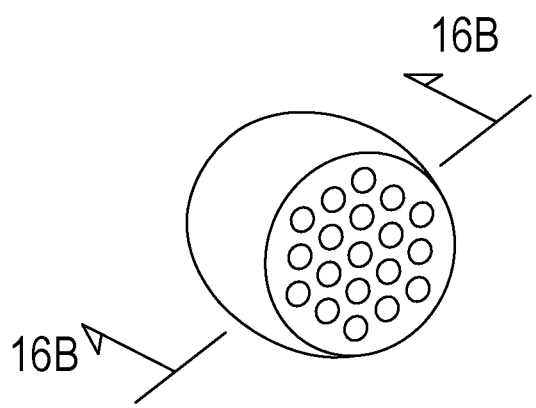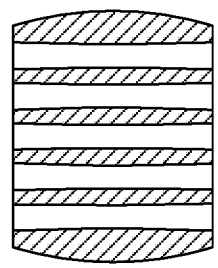
FIG. 16A        FIG. 16B
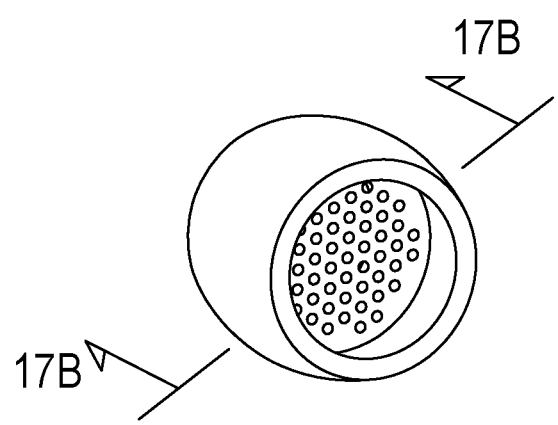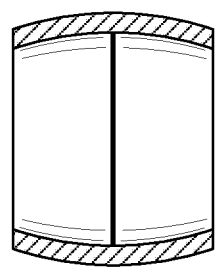
FIG. 17A        FIG. 17B

RESPIRATORY THERAPY INSTRUMENT OFFERING GAME-BASED INCENTIVES, TRAINING, AND TELEMETRY COLLECTION

CROSS REFERENCE TO RELATED APPLICATIONS

The present application is a U.S. nonprovisional patent application of, and claims priority under 35 U.S.C. § 119(e) to, U.S. provisional patent application Ser. No. 62/141,623, filed Apr. 1, 2015 and entitled "INSTRUMENT FOR ADAPTING RESPIRATORY THERAPY DEVICES FOR GAME-BASED INCENTIVES, TRAINING, AND TELEMETRY COLLECTION," which provisional patent application is expressly incorporated herein by reference. Additionally, a copy of U.S. provisional patent application Ser. No. 62/141,623 is attached hereto as Appendix A, which itself is expressly incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to respiratory therapy devices for pulmonary care, and, in particular, to respiratory therapy instruments and adapters that facilitate game-based incentives, training and telemetry collection.

Background

Respiratory therapy devices have long been used as an effective way for patients and medical professionals to understand and improve pulmonary function. One such respiratory therapy device is a clinical spirometer, which is commonly used to ascertain clinical measurements of lung function by assessing patient air flow during inhale and exhale. Other known respiratory therapy devices are generally more portable in nature and include devices such as incentive spirometry (IS) devices and positive expiratory pressure (PEP) devices. These portable devices have proven to be highly effective in the prevention and treatment of pulmonary complications such as pneumonia. An IS respiratory therapy device exercises a patient's lung function and utilizes an indicator to measure or quantify sustained inhalation vacuum. Patients are generally required to conduct several repetitions at intervals throughout the day. A PEP respiratory therapy device is designed to prolong the expiratory phase of normal breathing. Prolonging air expiration allows for a reduction in the respiratory rate and helps to facilitate a patient's capacity to mobilize airway secretions so that they can be coughed out and removed. Regular use of the PEP therapy device is generally encouraged as part of a treatment process.

Unfortunately, patients often do not use IS and PEP therapy devices correctly or as prescribed, which makes breathing exercises utilizing these devices much less effective. Caregivers must train patients to use these therapy devices in an effective manner and must encourage patients to undertake respiratory exercises using the therapy devices at appropriate intervals. However, even when caregivers take these measures, training and encouragement by caregivers can only accomplish so much. The burden ultimately falls upon the patient to use the therapy device effectively and at the prescribed intervals. Furthermore, even under circumstances where a patient follows the caregiver's instructions, it can be very difficult for the caregiver to receive accurate data that reflects the patient's use of these devices as well as device-specific treatment data, such as inhale volume.

Though clinical spirometers exist as an alternative to the afore-mentioned IS and PEP respiratory therapy devices, clinical spirometers introduce different complexities. A clinical spirometer can measure and report accurate patient data at the time of use, but such devices are often more complicated and generally require a trained clinician to operate. Additionally, the overall complexity of clinical spirometers tends to cut against their use as an effective preventative tool. Furthermore, because many clinical spirometers rely upon moving components (e.g., turbines) for pulmonary measurements, such devices can be associated with sanitation issues arising from repeated use. Damage to turbines can also be a choking hazard, especially to young patients.

Some known spirometry devices utilize data collection to improve efficacy of the respiratory treatment plan. U.S. Patent Application Publication No. US 2014/0100470 A1 to Perry discloses a digital spirometer system featuring a dedicated IS therapy device connected to a device capable of respiratory data collection and subsequent storage of the data in a database. The device includes an electronic display to provide instructions to a patient or to display measured data. U.S. Patent Application Publication No. US 2013/0066225 A1 to Kojouri discloses a monitoring IS therapy device system that measures inhalation/exhalation flow and/or volume data. Feedback based on the collected data is provided to the patient to facilitate compliance with a prescribed treatment plan and can also be provided to a monitoring station. Though both of these systems collect patient data for review by the patient or by the caregiver, neither takes additional measures to further incentivize a prescribed treatment plan, such as by the utilization of game-playing and/or other motivating factors. Furthermore, neither system utilizes a specialized flow sensor that might otherwise make these systems more useful and cost-effective as preventative solutions.

Another known spirometry device, described in U.S. Patent Application Publication No. US 2013/0303930 A1 to Elefteriades, et al., supports the concept of game-playing (i.e., gaming) within the context of incentive spirometry. The device incorporates a section of tubing that connects to an airflow transducer that converts the airflow to an analog voltage output, which can be further converted and transferred to a computer. With the extent of tubing required, the device is rather unwieldy, and it is not self-contained. Furthermore, as an IS-based device, the Elefteriades et al. device does not appear to be equipped for utility across multiple spirometry platforms, such as with PEP devices. And, as with other known systems, this device does not utilize a specialized flow sensor that might otherwise make the device more useful and cost-effective as a preventative solution.

Accordingly, there exists a need for improvements in the field of respiratory therapy devices that overcome shortcomings of existing technology. Furthermore, there exists a need for a device that is capable of use both as a preventative and as a treatment solution. These, and other needs, are addressed by one or more aspects of the present invention.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

Broadly defined, the present invention according to one aspect includes a respiratory therapy device adapter. The respiratory therapy device includes: a body having a grip and an airway tube; a pressure sensor adapted to detect pulmonary flow data from within the airway tube; and a circuit board housed within the body. The circuit board is configured to collect the pulmonary flow data detected by the pressure sensor. The circuit board is further configured to transmit data, including the collected pulmonary flow data, wirelessly to a computing device. The airway tube is adapted to be in fluid communication with a respiratory therapy device.

In features of this aspect, the grip may be a handheld grip; and/or the airway tube may be removable. In another feature of this aspect, the airway tube may be removably mounted to a clamp molded into the grip.

In other features of this aspect, the airway tube may be adapted to be in fluid communication with an IS respiratory therapy device; and/or the airway tube may be adapted to be in fluid communication with a PEP respiratory therapy device.

In another feature of this aspect, the airway tube may include a built-in IS respiratory therapy device.

In another feature of this aspect, the airway tube may include a built-in PEP respiratory therapy device.

In another feature of this aspect, the pressure sensor may be a gauge sensor.

In another feature of this aspect, the pressure sensor may be a differential sensor.

In another feature of this aspect, the pressure sensor may be an absolute sensor. In a further feature, the absolute pressure sensor may be calibrated periodically to account for ambient pressure changes.

In other features of this aspect, pulmonary flow data may be detected using a pressure-drop method; the pressure sensor may be adapted to detect pulmonary flow data during an inhale or an exhale; the transmitted data may further include power level data.

In another feature of this aspect, the circuit board may include a motion processing unit to collect device orientation data. In further features, the transmitted data may further include the collected device orientation data; the collected device orientation data may be utilized in determining whether to calibrate the pressure sensor; and/or the collected pulmonary flow data and the collected device orientation data may be utilized in game play for a game operated on the computing device.

In another feature of this aspect, the circuit board may include a database of R values corresponding with a range of respiratory therapy devices.

In another feature of this aspect, the computing device may include a database of R values corresponding with a range of respiratory therapy devices.

In another feature of this aspect, the computing device may download R values corresponding with a range of respiratory therapy devices from a networked server.

In another feature of this aspect, the computing device may include a laptop computer.

In another feature of this aspect, the computing device may include a game console.

In another feature of this aspect, the computing device may include a tablet computer.

In another feature of this aspect, the computing device may include a mobile telephone.

In another feature of this aspect, the circuit board may communicate electronically with the computing device to receive feedback data based on the transmitted data.

Broadly defined, the present invention according to another aspect includes a respiratory therapy device adapter substantially as shown and described.

Broadly defined, the present invention according to another aspect includes a method of adapting a respiratory therapy device for game-based incentives, training or data collection, substantially as shown and described.

Broadly defined, the present invention according to another aspect includes a respiratory therapy instrument providing a telehealth platform for pulmonary care. The respiratory therapy instrument includes a housing with opposed extension arms, an airway tube removably clamped between the opposed extension arms, a pair of pressure sensors, and a circuit board retained within the housing. The pair of pressure sensors is in communication with an interior of the airway tube and is configured to detect pulmonary flow data within the airway tube. The circuit board is configured to collect the pulmonary flow data detected by the pair of pressure sensors and includes a transmitter to send data, including the collected pulmonary flow data, wirelessly to a computing device. The collected pulmonary flow data is utilized in game play for an incentivization game operated on the computing device. The respiratory therapy instrument is configurable for use in a first configuration, whereby the respiratory therapy instrument operates to adapt an existing respiratory therapy device for telehealth functionality, or in a second configuration, whereby the respiratory therapy instrument operates as an independent respiratory therapy device with telehealth functionality.

In a feature of this aspect, when in use in the first configuration, the converted respiratory therapy device may be an incentive spirometry device.

In another feature of this aspect, when in use in the first configuration, the converted respiratory therapy device may a positive expiratory pressure device.

In another feature of this aspect, when in use in the second configuration, the respiratory therapy instrument may operate in a manner similar to a clinical spirometer.

In another feature of this aspect, when in use in the second configuration, the respiratory therapy instrument may operate in a manner similar to an incentive spirometry device.

In another feature of this aspect, when in use in the second configuration, the respiratory therapy instrument may operate in a manner similar to a positive expiratory pressure device.

In another feature of this aspect, at least one of the pair of pressure sensors may be a gauge sensor.

In another feature of this aspect, at least one of the pair of pressure sensors may be a differential sensor.

In another feature of this aspect, at least one of the pair of pressure sensors may be an absolute sensor.

In another feature of this aspect, the airway tube may be interchangeable with another airway tube of a different type.

In another feature of this aspect, when in use in the second configuration, the airway tube may include a flow resistance insert seated in an interior thereof between ports corresponding to the pair of pressure sensors such that pressure measurements are ascertainable upstream and downstream of the flow resistance insert. In a feature of this aspect, the flow resistance insert may be a Fleisch pneumatic insert. In another feature of this aspect, the flow resistance insert may be a Lilly pneumatic insert.

In another feature of this aspect, the circuit board may facilitate user access, via the computing device, to a database of resistance values corresponding with a plurality of flow resistance inserts in order to facilitate determination of a flow measurement through the airway tube and the flow resistance insert. In a feature of this aspect, the circuit board may include the database of resistance values. In another feature of this aspect, the computing device may include the database of resistance values.

In another feature of this aspect, when in use in the first configuration, the circuit board may facilitate user access, via the computing device, to a database of resistance values corresponding with a plurality of respiratory therapy devices in order to facilitate determination of a flow measurement through the airway tube and the respiratory therapy device.

In another feature of this aspect, the computing device may include a laptop computer.

In another feature of this aspect, the computing device may include a game console.

In another feature of this aspect, the computing device may include a tablet computer.

In another feature of this aspect, the computing device may include a mobile telephone.

In another feature of this aspect, the collected pulmonary flow data transmitted to the computing device may be stored with user-specific health records.

In another feature of this aspect, the housing may include a grip to facilitate holding the respiratory therapy instrument by hand.

Broadly defined, the present invention according to another aspect includes a respiratory therapy instrument providing a telehealth platform for pulmonary care. The respiratory therapy instrument includes a housing with opposed extension arms, an airway tube clamped between the opposed extension arms, at least one pressure sensor, and a circuit board retained within the housing. The at least one pressure sensor is in communication with an interior of the airway tube and is configured to detect pulmonary flow data within the airway tube, the at least one pressure sensor being substantially entirely free of moving components. The circuit board is configured to collect the pulmonary flow data detected by the at least one pressure sensor and includes a transmitter to send data, including the collected pulmonary flow data, wirelessly to a computing device. The collected pulmonary flow data is utilized in game play for an incentivization game operated on the computing device.

In a feature of this aspect, the at least one pressure sensor does not introduce additional resistance within the airway tube.

In another feature of this aspect, the at least one pressure sensor may include a gauge sensor.

In another feature of this aspect, the at least one pressure sensor may include a differential sensor.

In another feature of this aspect, the at least one pressure sensor may include an absolute sensor.

In features of this aspect, the at least one pressure sensor may be adapted to detect pulmonary flow data during an inhale or an exhale; and/or the housing may include a grip to facilitate holding the respiratory therapy instrument by hand.

Broadly defined, the present invention according to another aspect includes a respiratory therapy instrument providing a telehealth platform for pulmonary care. The respiratory therapy instrument includes a housing with opposed extension arms, an airway tube clamped between the opposed extension arms, at least one pressure sensor, and a circuit board retained within the housing. The at least one pressure sensor is in communication with an interior of the airway tube and is configured to detect pulmonary flow data within the airway tube. The circuit board includes a motion processing unit to detect motion data and is configured to collect the pulmonary flow data detected by the at least one pressure sensor and motion data detected by the motion processing unit. The circuit board includes a transmitter to send data, including the collected pulmonary flow data and motion data, wirelessly to a computing device.

In features of this aspect, the collected pulmonary flow data and motion data may be utilized in game play for an incentivization game operated on the computing device; the motion data detected by the motion processing unit may include step detection data for ascertaining a level of user exertion; the step detection data may include step count data; the motion data detected by the motion processing unit may include head tracking data; the motion data detected by the motion processing unit may include orientation data for ascertaining an orientation of the respiratory therapy instrument; the motion data detected by the motion processing unit may be used to establish automated wake and sleep cycles for the respiratory therapy instrument; and/or the housing may include a grip to facilitate holding the respiratory therapy instrument by hand.

Broadly defined, the present invention according to another aspect includes a respiratory therapy instrument providing a telehealth platform for pulmonary care. The respiratory therapy instrument includes a housing with opposed extension arms, an airway tube clamped between the opposed extension arms, at least one absolute pressure sensor, and a circuit board retained within the housing. The at least one absolute pressure sensor is in communication with an interior of the airway tube and is configured to detect pulmonary flow data within the airway tube. The circuit board is configured to collect the pulmonary flow data detected by the at least one absolute pressure sensor and includes a transmitter to send data, including the collected pulmonary flow data, wirelessly to a computing device. The at least one absolute pressure sensor is automatically calibrated at periodic intervals to account for measurement errors arising from changes in barometric pressure.

In features of this aspect, the circuit board may include a motion processing unit to detect motion data for confirming that the respiratory therapy instrument is not in use prior to commencement of a calibration cycle; and/or the housing may include a grip to facilitate holding the respiratory therapy instrument by hand.

Broadly defined, the present invention according to another aspect includes a respiratory therapy device adapter. The respiratory therapy device adapter includes a housing with opposed extension arms, an airway tube removably clamped between the opposed extension arms, a single pressure sensor, and a circuit board retained within the housing. The single pressure sensor is in communication with an interior of the airway tube and is configured to detect pulmonary flow data within the airway tube. The circuit board is configured to collect the pulmonary flow data detected by the single pressure sensor and includes a transmitter to send data, including the collected pulmonary flow data, wirelessly to a computing device. The collected pulmonary flow data is utilized in game play for an incentivization game operated on the computing device. The airway tube is in fluid communication with a respiratory therapy device, thereby converting the respiratory therapy device to an instrument with telehealth functionality.

In a feature of this aspect, the single pressure sensor may be a gauge sensor.

In another feature of this aspect, the single pressure sensor may be a differential sensor.

In another feature of this aspect, the single pressure sensor may be an absolute sensor.

In another feature of this aspect, the converted respiratory therapy device may be an incentive spirometry device.

In another feature of this aspect, the converted respiratory therapy device may be a positive expiratory pressure device.

In another feature of this aspect, the airway tube may be interchangeable with another airway tube of a different type.

In another feature of this aspect, the circuit board may facilitate user access, via the computing device, to a database of resistance values corresponding with a plurality of respiratory therapy devices in order to facilitate determination of a flow measurement through the airway tube and the respiratory therapy device. In a feature of this aspect, the circuit board may include the database of resistance values. In another feature of this aspect, the computing device may include the database of resistance values.

In another feature of this aspect, the computing device may include a laptop computer.

In another feature of this aspect, the computing device may include a game console.

In another feature of this aspect, the computing device may include a tablet computer.

In another feature of this aspect, the computing device may include a mobile telephone.

In another feature of this aspect, the housing may include a grip to facilitate holding the respiratory therapy device adapter by hand.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIG. 16A is a perspective view of a flow resistance insert capable of installation within the airway tubes of FIGS. 13 and 15;

FIG. 16B is a sectional view of the flow resistance insert of FIG. 16A, taken along line 16B-16B;

FIG. 17A is a perspective view of an alternative flow resistance insert capable of installation within the airway tubes of FIGS. 13 and 15;

FIG. 17B is a sectional view of the flow resistance insert of FIG. 17A, taken along line 17B-17B;

DETAILED DESCRIPTION

Figure 1:
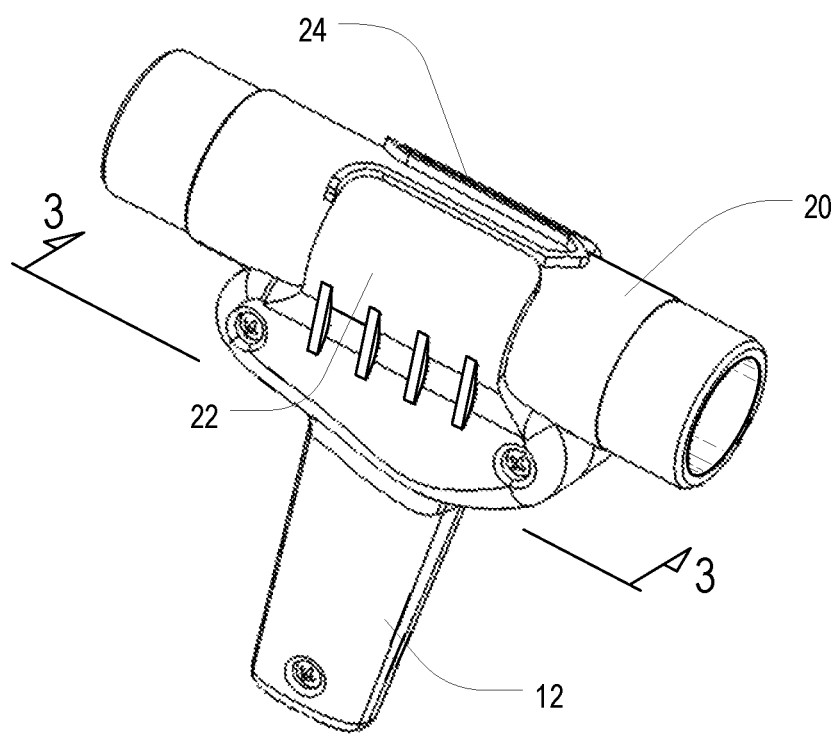
FIG. 1 is a perspective view of a respiratory therapy device adapter in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

As used herein, the term "respiratory therapy device" includes, but is not limited to, clinical spirometers, incentive spirometry (IS) devices, positive expiratory pressure (PEP) devices, inhalers, nebulizers and the like.

Figure 2:
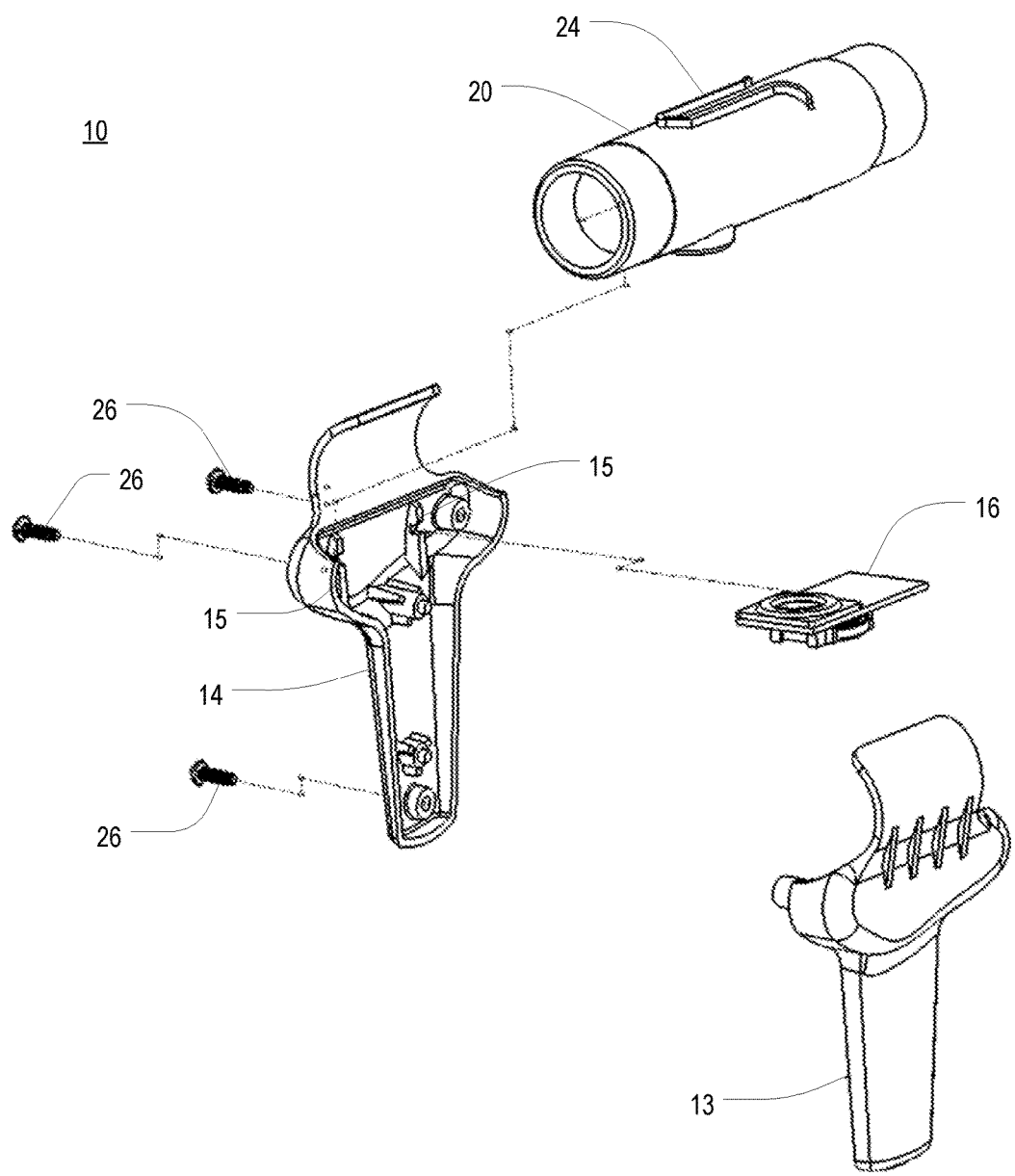
FIG. 2 is an exploded view of the respiratory therapy device adapter of FIG. 1.

FIG. 1 is a perspective view of a respiratory therapy device adapter 10 in accordance with one or more preferred embodiments of the present invention, and FIG. 2 is an exploded view of the adapter 10 of FIG. 1. As shown in FIGS. 1 and 2, the respiratory therapy device adapter 10 includes: a grip or housing 12, which is cast as two components 13,14; a circuit board 16 held within brackets 15 within the grip 12 and secured when the grip halves 13,14 are fastened together; and an airway tube 20 slid into a clamp 22 molded into the grip 12. The clamp 22 positions rails 24 that are molded into the airway tube 20 and correctly orients and seats the airway tube 20 relative to the grip 12 and circuit board 16. Though FIG. 1 shows the airway tube 20 clamped to the body of the adapter 10, it is contemplated that the airway tube 20 can be attached by a variety of different mechanisms.

It is contemplated that the adapter 10 is attachable to a wide variety of different respiratory therapy devices, including IS and PEP therapy devices but also inhalers, nebulizers and the like. Some contemplated respiratory therapy devices that are capable of use with the adapter 10 include the Coach2® Incentive Spirometer, manufactured by Smiths Medical ASD, Inc. of St. Paul, Minn., USA, the Hudson RCI® Lung Volume Exerciser Incentive Spirometer, manufactured by Teleflex Incorporated of Wayne, Pa., USA, and the Acapella® DM & DH Vibratory PEP Therapy System, manufactured by Smiths Medical ASD, Inc. of St. Paul, Minn., USA.

It is contemplated that the grip components 13,14 can be fastened together in a variety of different ways. In one contemplated embodiment, the grip components 13,14 are fastened together using separate fasteners, such as screws 26. In another contemplated embodiment, the grip components 13,14 are snap-fit to one another. In still another contemplated embodiment, the grip components 13,14 are held together with an elastic band. In this particular embodiment, the size of the elastic band that is used to fasten the grip components 13,14 together is selected to suit the size of a patient's hands. In such manner, a standard molded grip can be customized with suitable elastic bands to meet the specific needs of a target patient (with sizes ranging from a small child to an adult).

The airway tube 20 is removable from the grip 12, which facilitates ease of cleaning or swapping with different airway tubes having differing functions. In contemplated embodiments, an airway tube may have a built-in IS or PEP respiratory therapy device, thereby eliminating the need for a separate IS or PEP respiratory therapy device. It is further contemplated that the airway tube may be exchanged for an IS airway tube, PEP airway tube, or clinical spirometer airway tube. Still further, it is contemplated that a precision pressure-drop or other type of flow sensor could be added to the airway tube in order to provide more precise clinical pulmonary measurements.

It is contemplated that the airway tube 20 for use with the respiratory therapy device adapter 10 can be assembled in a variety of ways. In one contemplated embodiment, the airway tube is assembled from multiple components. In another contemplated embodiment, the airway tube 20 is a unitary structure molded from a single cast, as shown in FIG.

2. It is further contemplated that the airway tube 20 may be hollow or may contain a laminar flow section within the tube.

Figure 3:
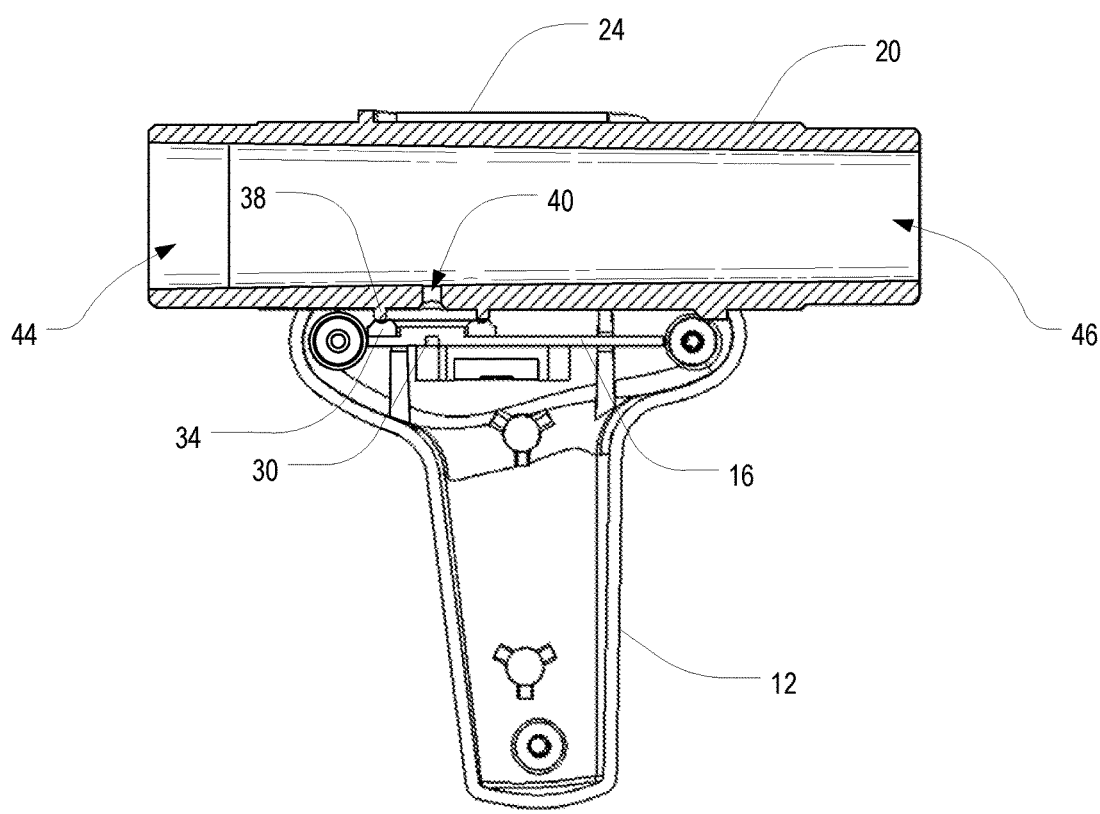
FIG. 3 is a sectional view of the respiratory therapy device adapter of FIG. 1, taken along line 3-3.

FIG. 3 is a sectional view of the adapter 10 of FIG. 1, taken along line 3-3. Pressure within the airway tube 20 is measured using a pressure sensor 30. It is contemplated that the pressure sensor 30 may be of any type, including gauge, absolute, or differential sensors. A gasket 34 is disposed between the circuit board 16 and an airway tube flange 38, and an airway port 40 in fluid communication with the airway tube 20 is securely sealed to the pressure sensor 30. In this way, the pressure sensor 30 can measure pressure within the airway tube 20 during an inhale or exhale. When the airway tube 20 is inserted into the grip 12 a press fit between the tube flange 38, gasket 34, and pressure sensor 30 can be achieved by an outward force exerted on the clamp 22 by the installed airway tube 20. Tapered inlet 44 and outlet sections 46 of the airway tube 20 facilitate attachment of mouthpieces and respiratory therapy devices respiratory therapy device adapter 10.

The circuit board 16 collects and digitizes pulmonary flow telemetry. The circuit board 16 also includes onboard sensing for detecting the orientation and movement of the adapter 10. It is contemplated that the ability to sense motion can take the form of a motion processing unit (MPU) integrated into the circuit board 16. Orientation data may be used to track the position of the adapter 10 while held in the hand or in a mount. Movement detection can be used for establishing automated wake and sleep cycles for the adapter 10 as well as for detecting when to calibrate the pressure sensor 30 of the adapter 10 (as discussed in greater detail below).

In some contemplated embodiments, the MPU can be used for purposes of head tracking, which may be used as a positioning input for games. Furthermore, in some contemplated embodiments, the MPU can be used for purposes of step detection. Spirometry measurements using a clinical spirometer are oftentimes taken in connection with or following a period of user exercise. Inclusion of step detection capability in the respiratory therapy instrument 10, via the MPU, can facilitate measuring or quantifying a level of exertion immediately prior to a flow measurement. In use, a patient need only keep the respiratory therapy instrument 10 on his or her person during exercise so that the MPU can measure or quantify the user's level of exertion. It is contemplated that step detection measurements include, but are not limited to, counting steps and determination of the pace of user movement (e.g., running, jogging, or walking).

Figure 4:
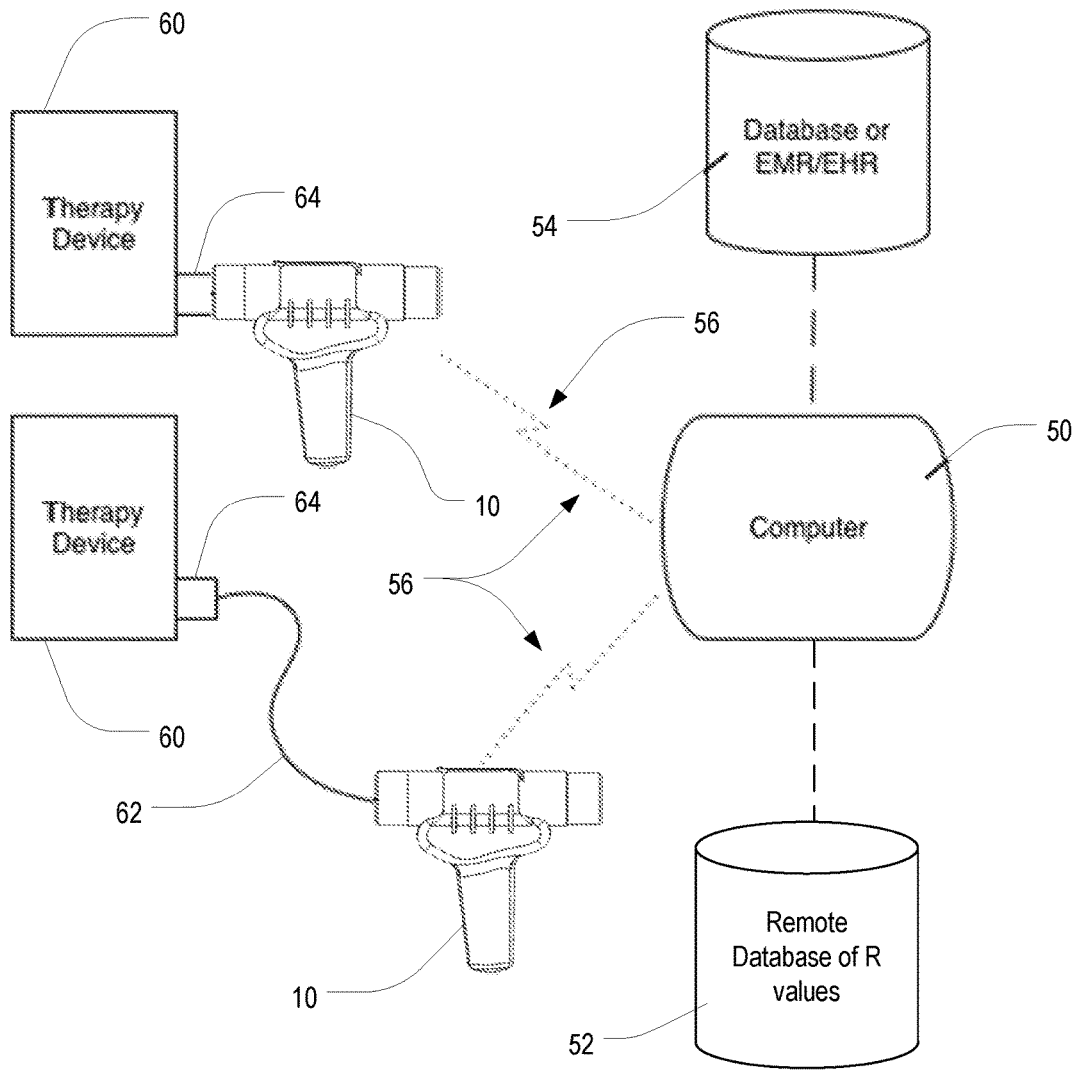
FIG. 4 is a schematic view of a system for transmitting wireless telemetry retrieved by the respiratory therapy device adapter of FIG. 1 to a computing device.
Figure 5:
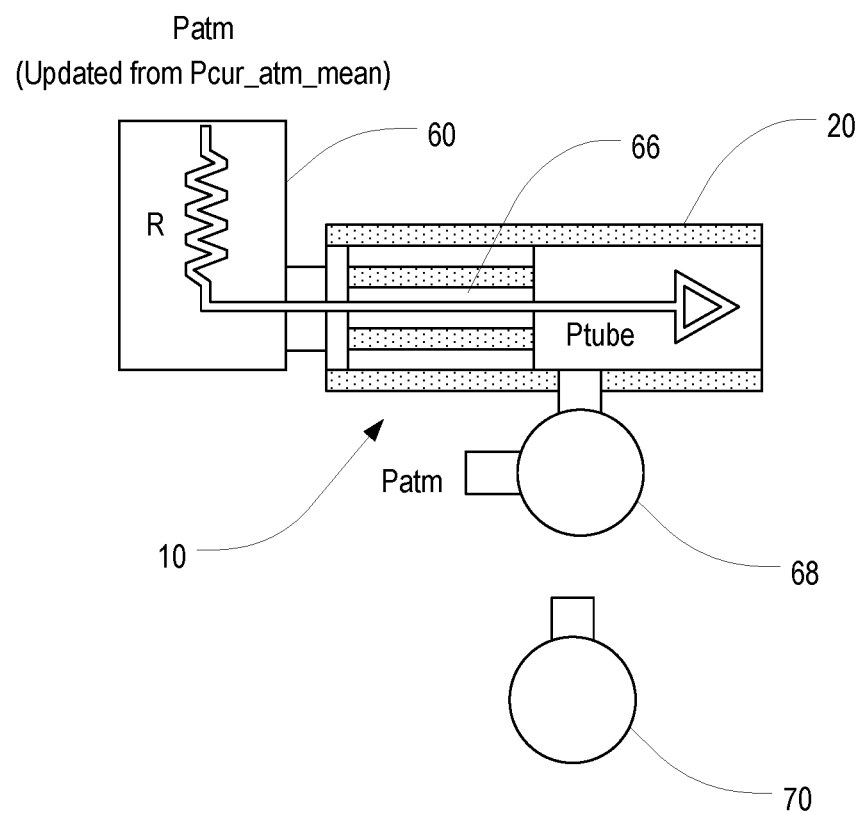
FIG. 5 is a schematic view of a system for measuring pressure and/or flow within the airway of a respiratory therapy device equipped with the respiratory therapy device adapter of FIG. 1.

FIG. 4 is a schematic view of a system for transmitting wireless telemetry retrieved by the adapter 10 of FIG. 1 to a computing device 50. FIG. 5 is a schematic view of a system for measuring pressure and/or flow within the airway of a respiratory therapy device 60 equipped with the adapter 10 of FIG. 1. As depicted in FIG. 4, it is contemplated that the respiratory therapy device adapter 10 can attach to the therapy device 60 either using a flexible hose 62 or directly to a port 64 of the therapy device 60.

With reference to FIG. 5, flow sensing is accomplished using a pressure-drop method that is similar to a Fleisch or Lilly tube. The pressure drop across the therapy device 60 can be determined by subtracting the local atmospheric pressure ($P_{atm}$) at the outlet of the therapy device 60 from the pressure within the airway tube 20 ($P_{tube}$). Because flow resistance (R) of existing therapy devices is generally a known value (whether by laboratory testing or by testing with a patient using a known flow rate), the flow rate through the therapy device 60 and the airway tube 20 of the adapter 10 can be determined. In this manner, the therapy device itself can be used as a calibrated flow resistance. Flow resistance of the therapy device 60 is therefore able to be used as a standard across which a pressure differential (dP) is measured using differential/gauge 68 or absolute 70 pressure sensors, where $dP=P_{atm}-P_{tube}$. R values can be provided by a database of such values that correspond with a wide selection of therapy devices, as discussed in more detail below. As depicted in FIG. 5, it is contemplated that, in at least some embodiments, a laminar flow section 66 in the form of tubes or a screen may also be included in the airway tube 20. This laminar flow section would add an additional pneumatic resistance $R_{lf}$, which would be added to the flow resistance (R) of the therapy device.

The design of the pressure sensor 30 is such that additional resistance is not introduced into the airway. This can be advantageous when the adapter 10 is used with IS and PEP therapy devices, as significant resistance to the airway can be avoided when these devices are attached. Furthermore, because sensing activity using the pressure sensor 30 does not require moving parts, the risk of choking hazards and other safety concerns can be mitigated or eliminated.

In one contemplated embodiment, the pressure sensor 30 of the adapter 10 is a commercial absolute pressure sensor. One such commercial absolute pressure sensor available on the market is the MPL3115 absolute pressure sensor (designated as an altimeter), which is manufactured by Freescale Semiconductor Inc. of Austin, Tex., USA. When using an absolute pressure sensor, flow offset errors arising from changes in the local atmospheric pressure due to changing weather or altitude can be reduced or avoided entirely through continuous calibration of the absolute sensor.

In the case of an absolute pressure sensor, continuous calibration of the absolute pressure sensor whenever the adapter 10 is not in use (as detected by the MPU) can remove flow measurement errors arising from changes in barometric pressure due to weather patterns, elevation changes (such as by moving in an elevator) that might otherwise appear as a signal. Small flow bias can lead to large errors in calculation of total inhale volume, since inhale volume is a summation of instantaneous airway flow.

It is contemplated that flow bias for an absolute pressure sensor can be resolved by continuously (such as every 5 seconds) waking the adapter 30 and checking to see if the adapter 10 has been still since the last measurement (as detected by the MPU). Orientation of the adapter 10 can be assessed in the same manner. If the adapter 30 is still and not in an orientation implying that it is in use, then a series of local atmospheric measurements can be taken and a mean ($P_{cur\_atm\_mean}$) and standard deviation ($P_{cur\_atm\_std}$) can be calculated and stored. $P_{atm}$ is then set to the updated $P_{cur\_atm\_mean}$. Any changes in differential pressure ($dP=P_{atm}-P_{tube}$) that are smaller than some multiple of $P_{cur\_atm\_std}$ can be ignored. This process establishes a noise threshold that is dependent upon the local atmospheric conditions. In this way, as the adapter 10 is transported or as weather changes, the local atmosphere ($P_{atm}$ in FIG. 5) is continuously updated, thereby minimizing bias in the calculated pressure drop (dP) when the flow calculation is actually made.

A database of flow resistance (R) values 52 for a selection of therapy devices is available either onboard the circuit board 16 or through a wireless connection to a computing device 50 or from a networked server. The user selects the correct device from a computer screen, and firmware for the adapter 10 selects the appropriate R value from the database 52.

As depicted in FIG. 4, the circuit board of each adapter 10 also includes a transmitter, such as a radio, for sending wireless telemetry 56 to a computing device 50. This telemetry 56 may include, among other things, pulmonary data, power level data, step counts, or device orientation data. Data may also be stored locally on the adapter 10 for download to a database of electronic medical records (EMR) or electronic health records (EHR) 54 through the computing device 50. It is contemplated that the computing device 50 may be local to the user or remote. It is further contemplated that the computing device 50 can be any of a wide range of devices that include desktop computers, laptop computers, game consoles, mobile devices (such as a phone or tablet computer), and the like. The computing device 50 may be used for gaming, to provide the patient with training and real time feedback, to collect telemetry or other data, and to store R values for a variety of therapy devices.

Utilizing the adapter 10 with games and gaming techniques provides a fast and easy way to keep patients interested in performing their exercises. Push alerts on the associated computing device remind patients when they need to perform an exercise. Taking advantage of attributes of the circuit board 16, including the MPU with head tracking and/or step detection, the adapter 10 can be utilized as a game controller, with the patient's breathing exercises being used to accomplish certain tasks within the game. It is contemplated that selected air flow targets (as established by the caregiver) can be indicated by LEDs or audio outputs on the adapter itself as part of the game.

Within the game, real time feedback is used to guide each exercise. Training videos included in the game instruct the patient on how to setup and perform the exercise. Telemetry 56 from each exercise is saved on the computing device 50 and sent to a server 54 where it can be included in a patient's medical/health records. Processed data can inform caregivers whether the patent has been following the prescribed exercises as well as the quality (and trends) of the exercises. From this analysis, a caregiver can assess the efficacy of the prescribed treatment. It is further contemplated that collected data may be analyzed to detect coughing or wheezing that may be indicators for respiratory distress.

The adapter 10 helps to reduce the rates of pneumonia and other pulmonary complications in at-risk populations by converting existing respiratory therapy devices to telehealth platforms that use gaming and alerts to incentivize patients to follow their prescribed therapy and collect data to report compliance and treatment efficacy back to caregivers. When combined with an existing respiratory therapy device, the adapter 10 is part of a system that, among other things, facilitates patients being alerted by the computing device 50 when to perform their therapy based on a prescribed frequency or based on prior use data, incentivizes patients to use their therapy through gaming, trains patients in the proper use of their therapy devices using real-time feedback within the game, and reports back to the doctor or other caregiver compliance and pulmonary health trends. It is contemplated that the adapter 10 is usable both as a preventative and as a treatment for pulmonary complications in chronic (long term such as nursing home) and acute (short-term such as post-operative) populations.

Implementation of the adapter 10 with existing respiratory therapy devices, including IS and PEP therapy devices, improves these devices by, among other things, automating patient training and coaching, automating data reporting; incentivizing use of the therapy device, and/or facilitating the collection of total inhale/exhale volume for therapy devices that do not have such a measure.

Figure 6:
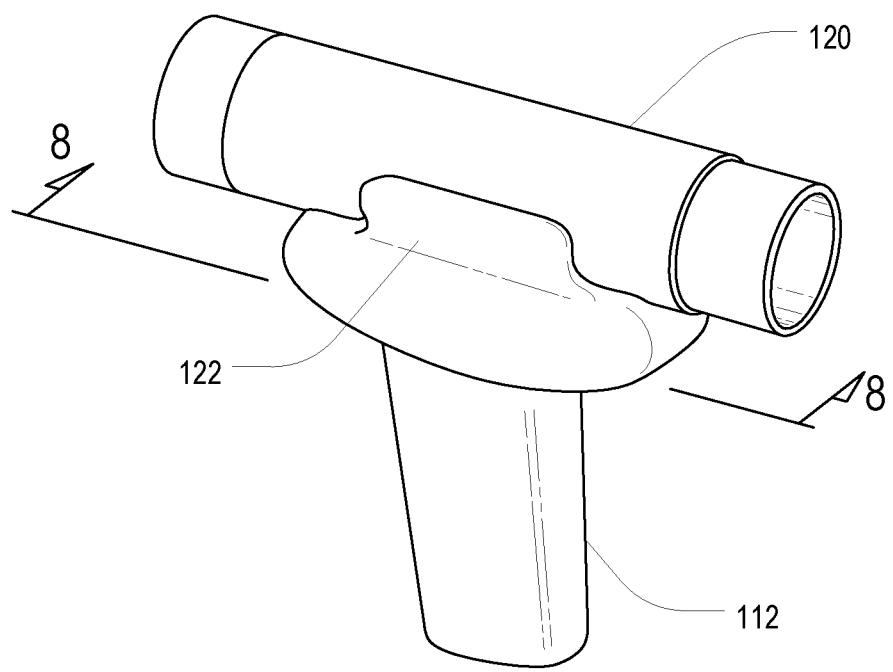
FIG. 6 is a perspective view of an alternative respiratory therapy device adapter in accordance with one or more preferred embodiments of the present invention.
Figure 7:
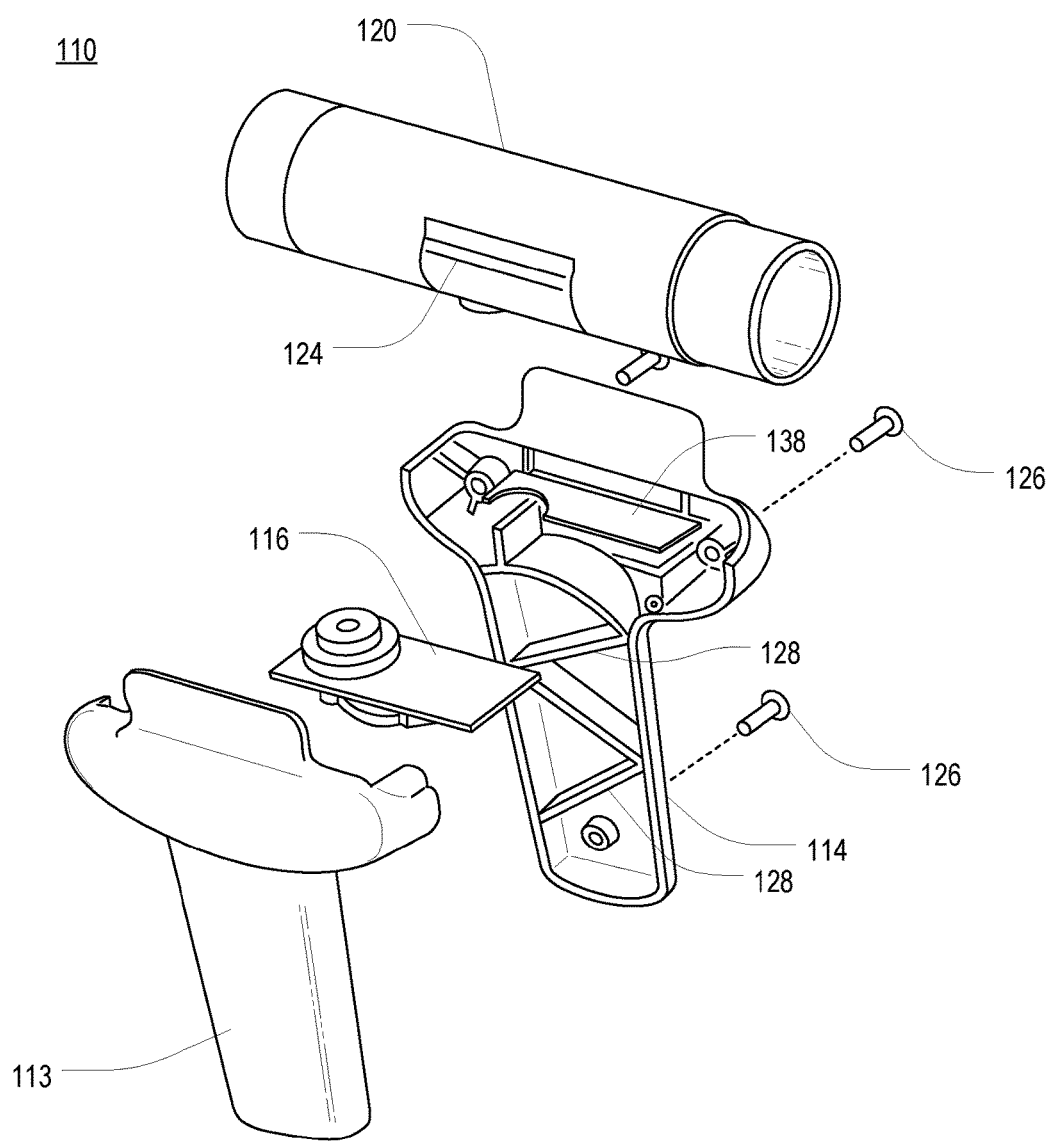
FIG. 7 is an exploded view of the respiratory therapy device adapter of FIG. 6.

FIG. 6 is a perspective view of an alternative respiratory therapy device adapter 110 in accordance with one or more preferred embodiments of the present invention, and FIG. 7 is an exploded view of the respiratory therapy device adapter 110 of FIG. 6. The respiratory therapy device adapter 110 of FIGS. 6 and 7 is similar in form to the respiratory therapy device adapter 10 discussed above in connection with FIGS. 1-5, but with various structural differences that can provide additional advantages during assembly and use. As shown in FIGS. 6 and 7, the respiratory therapy device adapter 110 includes: a grip or housing 112, which is cast as two components 113,114; a circuit board 116 held within the grip 112 and secured when the grip halves 113,114 are fastened together; and an airway tube 120 accommodated within a clamp 122 molded into the grip 112. The clamp 122 engages corresponding grooves 124 that are molded into the airway tube 120 at both sides thereof and correctly orients and seats the airway tube 120 relative to the grip 112 and circuit board 116. Though FIG. 6 shows the airway tube 120 clamped to the body of the adapter 110, it is contemplated that the airway tube 120 can be attached by a variety of different mechanisms.

It is contemplated that the adapter 110 is attachable to a wide variety of different respiratory therapy devices, including IS and PEP therapy devices, but also inhalers, nebulizers and the like. Some contemplated respiratory therapy devices that are capable of use with the adapter 110 include the Coach2® Incentive Spirometer, manufactured by Smiths Medical ASD, Inc. of St. Paul, Minn., USA, the Hudson RCI® Lung Volume Exerciser Incentive Spirometer, manufactured by Teleflex Incorporated of Wayne, Pa., USA, and the Acapella® DM & DH Vibratory PEP Therapy System, manufactured by Smiths Medical ASD, Inc. of St. Paul, Minn., USA.

As shown in FIG. 7, the grip components 113,114 are molded to include a reinforced interior construction characterized by a series of reinforcement walls or ribs 128. Such interior geometry provided by the ribs 128 can enhance the strength and rigidity of the grip 112 after assembly. It is contemplated that the grip components 113,114 can be fastened together in a variety of different ways. In one contemplated embodiment, the grip components 113,114 are fastened together using separate fasteners, such as screws 126. In another contemplated embodiment, the grip components 113,114 are snap-fit to one another. In still another contemplated embodiment, the grip components 113,114 are held together with an elastic band. In this particular embodiment, the size of the elastic band that is used to fasten the grip components 113,114 together is selected to suit the size of a patient's hands. In such manner, it is contemplated that a standard molded grip can be customized with suitable elastic bands to meet the specific needs of a target patient (with sizes ranging from a small child to an adult).

The airway tube 120 is removable from the grip 112, which facilitates ease of cleaning or swapping with different airway tubes having differing functions. Removal of the airway tube 120 can be accomplished by unseating the outer edges of the clamp 122 from the grooves disposed at sides of the airway tube 120. In contemplated embodiments, an airway tube may have a built-in IS or PEP respiratory therapy device, thereby eliminating the need for a separate IS or PEP respiratory therapy device. It is further contemplated that the airway tube may be exchanged for an IS airway tube, PEP airway tube, or clinical spirometer airway tube. The clinical spirometer airway tube can include a laminar flow section (such as the laminar flow section 66 depicted in FIG. 5) providing a calibrated pneumatic resistance ($R_{tf}$) that may be used as a precision pressure drop flow sensor.

It is contemplated that the airway tube 120 for use with the respiratory therapy device adapter 110 can be assembled in a variety of ways. In one contemplated embodiment, the airway tube is assembled from multiple components. In another contemplated embodiment, the airway tube 120 is a unitary structure molded from a single cast, as shown in FIG. 7. It is further contemplated that the airway tube 120 may be hollow or may contain a laminar flow section within the tube.

Figure 8:
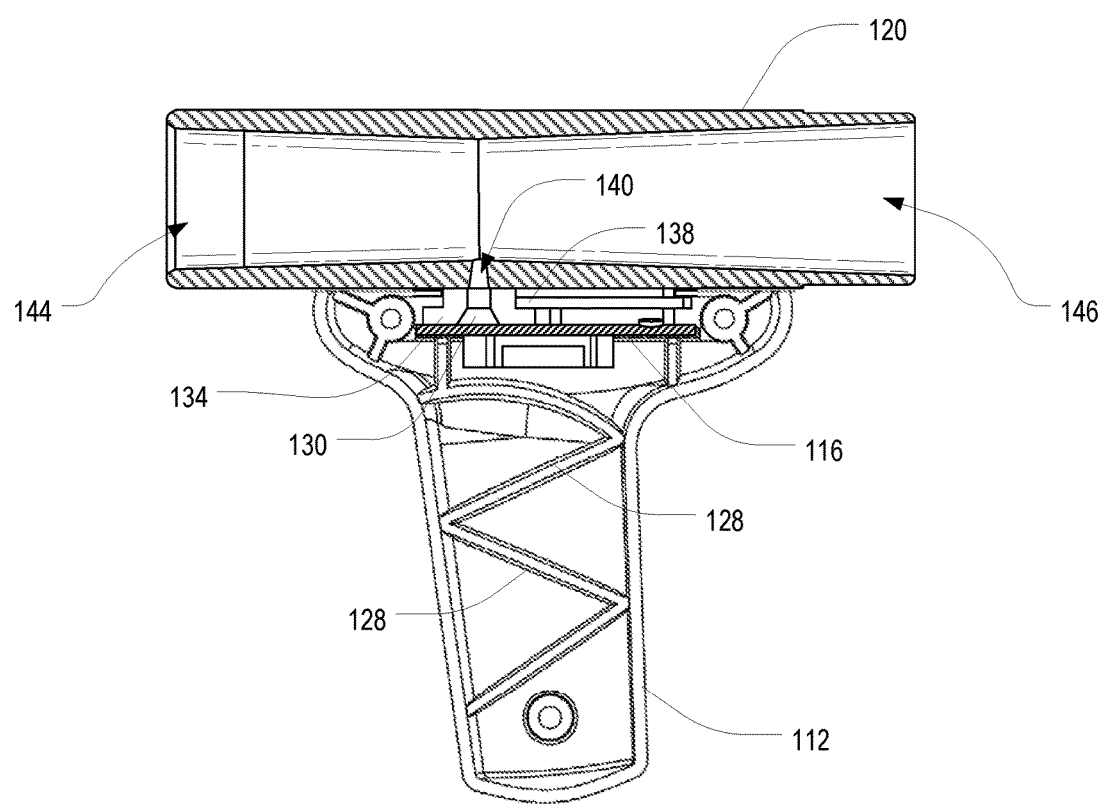
FIG. 8 is a sectional view of the respiratory therapy device adapter of FIG. 6, taken along line 8-8.

FIG. 8 is a sectional view of the respiratory therapy device adapter 110 of FIG. 6, taken along line 8-8. Pressure within the airway tube 120 is measured using a pressure sensor 130. It is contemplated that the pressure sensor 130 may be of any type, including gauge, absolute, or differential sensors. A gasket 134 is disposed between the circuit board 116 and a retaining flange 138, and an airway port 140 in fluid communication with the airway tube 120 is securely sealed to the pressure sensor 116. In this way, the pressure sensor 130 can measure the pressure within the airway tube 120 during an inhale or exhale. When the airway tube 120 is inserted into the grip 112 a press fit between the retaining flange 138, gasket 134, and pressure sensor 116 can be achieved by an outward force exerted on the clamp 122 by the installed airway tube 120. Tapered inlet 144 and outlet sections 146 of the airway tube 120 facilitate attachment of mouthpieces and respiratory therapy devices to the respiratory therapy device adapter 110.

Operation and functionality of the respiratory therapy device adapter 110 of FIGS. 6-8, including use of the device adapter 110 in flow sensing, motion detection, telemetry data collection and transmission, and incentivization of use through game-playing, are similar to or the same as that which is previously set forth above in connection with the respiratory therapy device adapter 10 of FIGS. 1-5. Implementation of the adapter 110 with existing respiratory therapy devices, including IS and PEP therapy devices, improves these devices by, among other things, automating patient training and coaching, automating data reporting; incentivizing use of the therapy device, and/or facilitating the collection of total inhale/exhale volume for therapy devices that do not have such a measure.

Figure 9:
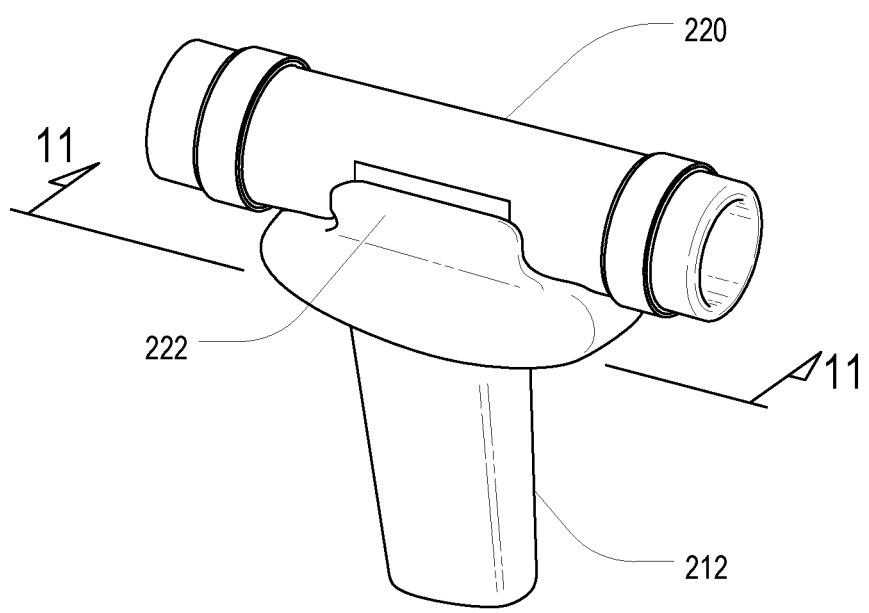
FIG. 9 is a perspective view of a respiratory therapy instrument in accordance with one or more preferred embodiments of the present invention.
Figure 10:
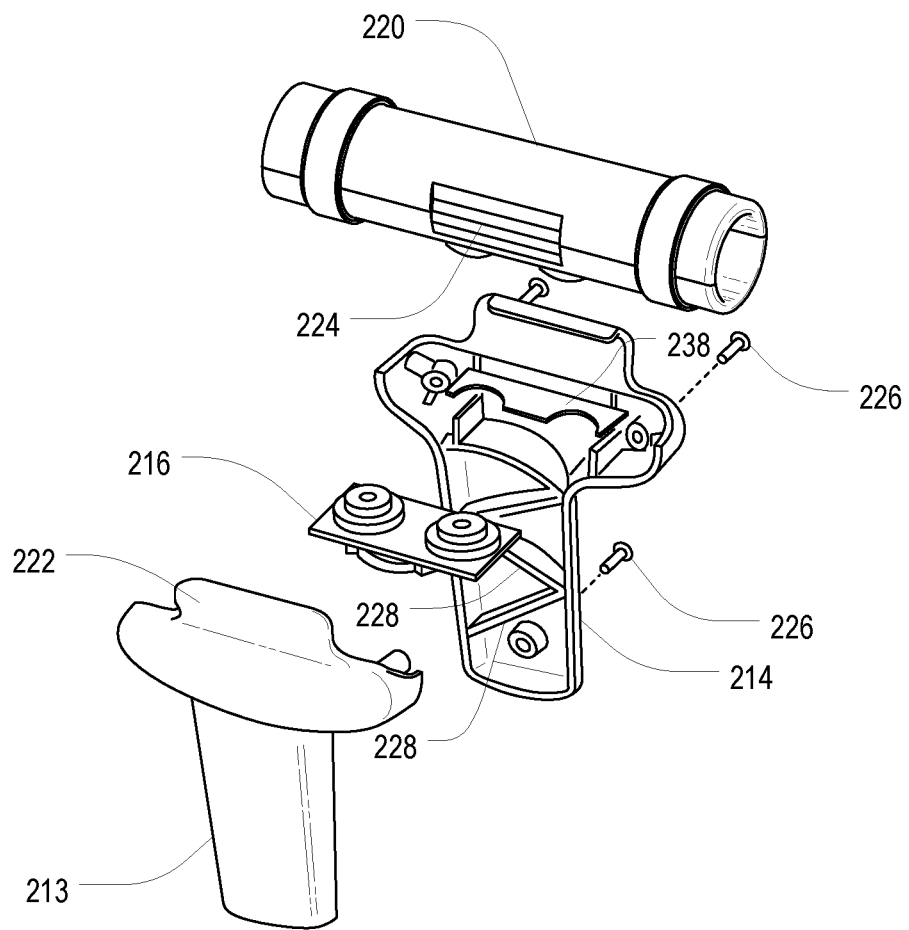
FIG. 10 is an exploded view of the respiratory therapy instrument of FIG. 9.

FIG. 9 is a perspective view of a respiratory therapy instrument 210 in accordance with one or more preferred embodiments of the present invention, FIG. 10 is an exploded view of the respiratory therapy instrument 210 of FIG. 9. The respiratory therapy instrument 210 of FIGS. 9 and 10 is similar in some respects to the respiratory therapy device adapters 10,110 discussed above in connection with FIGS. 1-8, but with various structural differences that can provide additional advantages during assembly and use. Additionally, as will be explained in greater detail below, the respiratory therapy instrument 210 of FIGS. 9 and 10 includes a pair of pressure sensors and is capable of use either as an adapter attachable to a wide variety of different respiratory therapy devices or as a stand-alone respiratory therapy device that can function in a manner similar to a clinical spirometer or other clinical instrument.

When in use as an adapter, it is contemplated that the instrument 210 is attachable to a wide variety of different respiratory therapy devices, including IS and PEP therapy devices but also inhalers, nebulizers and the like. Some contemplated respiratory therapy devices that are capable of use with the instrument 210 include the Coach2® Incentive Spirometer, manufactured by Smiths Medical ASD, Inc. of St. Paul, Minn., USA, the Hudson RCI® Lung Volume Exerciser Incentive Spirometer, manufactured by Teleflex Incorporated of Wayne, Pa., USA, and the Acapella® DM & DH Vibratory PEP Therapy System, manufactured by Smiths Medical ASD, Inc. of St. Paul, Minn., USA.

As shown in FIGS. 9 and 10, the respiratory therapy instrument 210 includes: a grip or housing 212, which is cast as two components 213,214; a circuit board 216 held within the grip 212 and secured when the grip halves 213,214 are fastened together; and an airway tube 220 accommodated within a clamp 222 molded into the grip 212. The clamp 222 engages corresponding grooves 223,224 that are molded into the airway tube 220 at both sides thereof and correctly orients and seats the airway tube 220 relative to the grip 212 and circuit board 216. Though FIG. 9 shows the airway tube 220 clamped to the body of the instrument 210, it is contemplated that the airway tube 220 can be attached by a variety of different mechanisms.

As shown in FIG. 10, the grip components 213,214 are molded to include a reinforced interior construction characterized by a series of reinforcement walls or ribs 228. Such interior geometry provided by the ribs 228 can enhance the strength and rigidity of the grip 212 after assembly. It is contemplated that the grip components 213,214 can be fastened together in a variety of different ways. In one contemplated embodiment, the grip components 213,214 are fastened together using separate fasteners, such as screws 226. In another contemplated embodiment, the grip components 213,214 are snap-fit to one another. In still another contemplated embodiment, the grip components 213,214 are held together with an elastic band. In this particular embodiment, the size of the elastic band that is used to fasten the grip components 213,214 together is selected to suit the size of a patient's hands. In such manner, it is contemplated that a standard molded grip can be customized with suitable elastic bands to meet the specific needs of a target patient (with sizes ranging from a small child to an adult).

The airway tube 220 is removable from the grip 212, which facilitates ease of cleaning or swapping with different airway tubes having differing functions. Removal of the airway tube 220 can be accomplished by unseating the outer edges of the clamp 222 from the grooves disposed at sides of the airway tube 220. In contemplated embodiments, the airway tube may be exchanged for an IS airway tube, PEP airway tube, or clinical spirometer airway tube.

Figure 11:
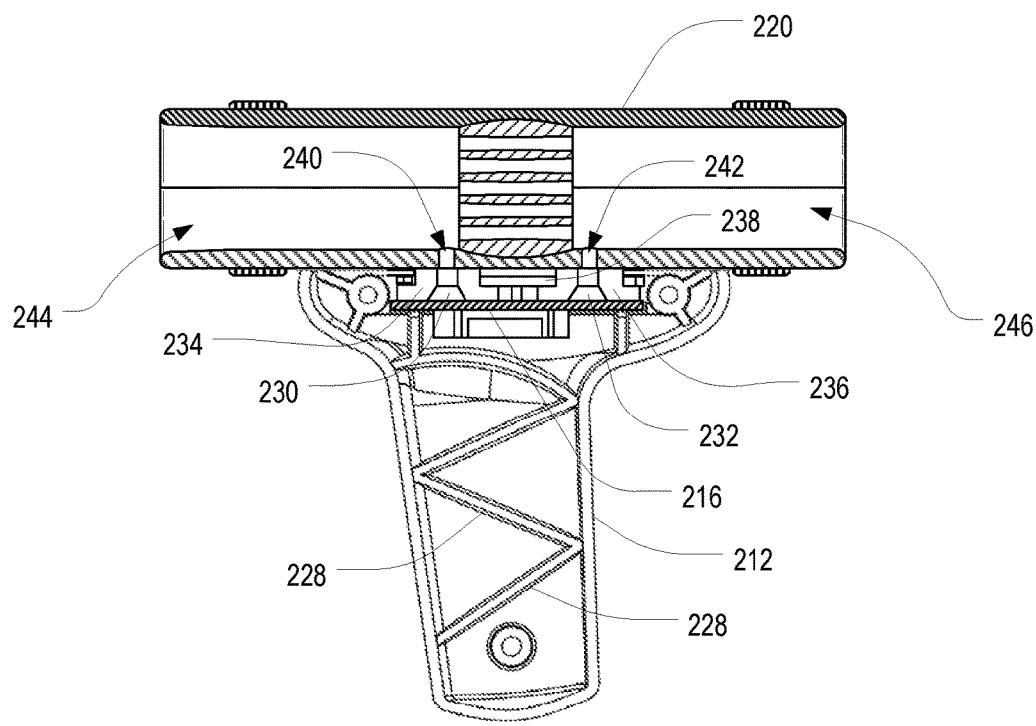
FIG. 11 is a sectional view of the respiratory therapy instrument of FIG. 9, taken along line 11-11.

FIG. 11 is a sectional view of the respiratory therapy instrument 210 of FIG. 9, taken along line 11-11. Unlike the airway tubes 20,120 described above in connection with FIGS. 1-8, the airway tube 220 of the respiratory therapy instrument 210 is equipped to accommodate a pair of pressure sensors 230,232, each with a corresponding airway port 240,242 in fluid communication with the airway tube 220 to facilitate detection of flow data within the airway tube 220. It is contemplated that pressure within the airway tube 220 can be measured using either or both pressure sensors 230,232. The sensors may be of any type, including gauge, absolute, or differential sensors. Gaskets 234,236 are disposed between the circuit board 216 and a retaining flange 238 so that the airway ports 240,242 are securely sealed to the corresponding pressure sensor 230,232. In this way, the pressure sensors 230,232 can be configured to measure the pressure within the airway tube 220 during an inhale or exhale. When the airway tube 220 is inserted into the grip 212 a press fit between the retaining flange 238, the gaskets 234,236, and the pressure sensors 230,232 can be achieved by an outward force exerted on the clamp 222 by the installed airway tube 220. Tapered inlet 244 and outlet sections 246 of the airway tube 220 facilitate attachment of mouthpieces and respiratory therapy devices to the respiratory therapy instrument 210.

Figure 12A:
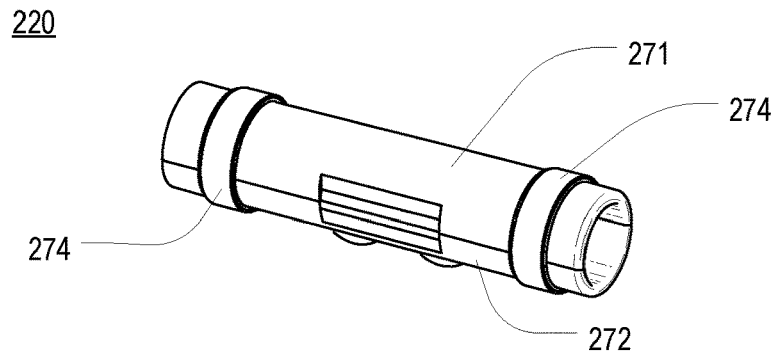
FIG. 12A is a perspective view of the airway tube of the respiratory therapy instrument of FIG. 9.
Figure 12B:
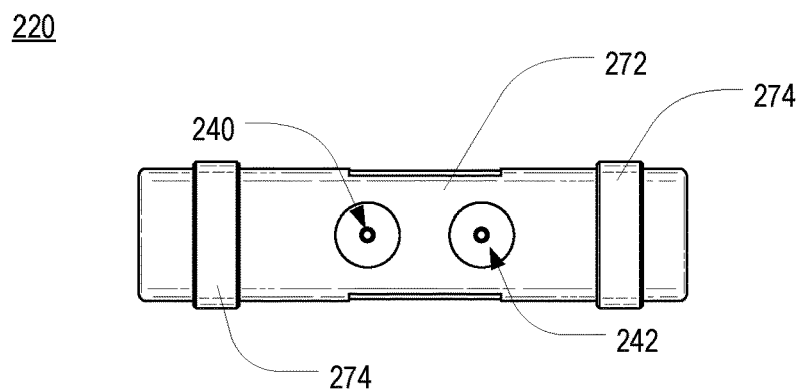
FIGS. 12B and 12C are bottom and end views, respectively, of the airway tube of FIG. 12A.
Figure 12C:
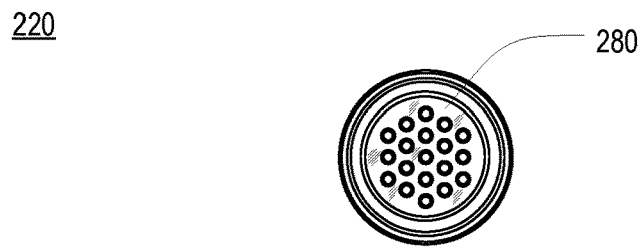
Figure 13:
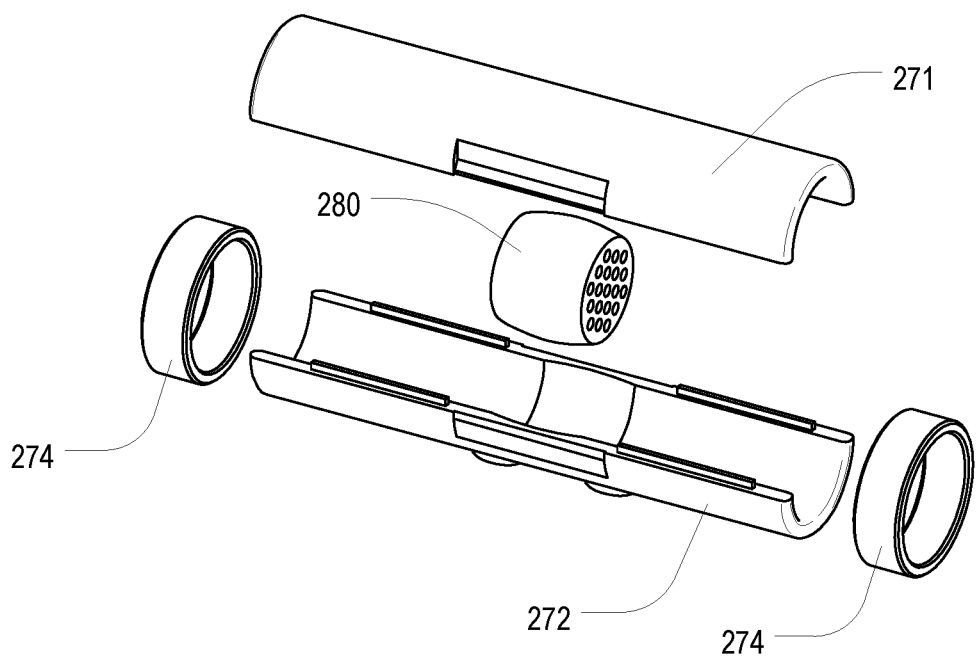
FIG. 13 is an exploded view of the airway tube of FIG. 12A, depicting a flow resistance insert contained within the airway tube.

It is contemplated that the airway tube 220 for use with the respiratory therapy instrument 210 can be assembled in a variety of ways. In one embodiment, depicted in FIGS. 12A-12C and 13, the airway tube 220 is assembled from upper and lower tube sections 271,272 that are held together with a pair of collars 274. In this regard, FIG. 12A is a perspective view of the airway tube 220 of the respiratory therapy instrument 210 of FIG. 9, and FIGS. 12B and 12C are bottom and end views, respectively, of the airway tube 220 of FIG. 12A. FIG. 13 is an exploded view of the airway tube 220 of FIG. 12A, depicting a flow resistance insert 280 contained within the airway tube 220. It is contemplated that the upper and lower tube sections 271,272 can be permanently bonded to one another using adhesive or welds. It is further contemplated that the upper and lower tube sections 271,272 can be paired to one another in a non-permanent way so as to permit a user to be able to change or replace the flow resistance insert 280 held within an interior of the airway tube 220.

For example, it is contemplated that the upper and lower tube sections 271,272 can be paired together with tapered collars 274 slid onto either end of the combined sections to retain them in a paired relationship. The tapered shape of the collars 274 allows the collars to be tightened into position manually by sliding them toward a center of the airway tube 220, thereby helping to establish an airtight fit between the sections. Still further, it is contemplated that the upper and lower tube sections 271,272 can include recesses to receive the collars 274, thereby helping to retain the collars in a desired location along the length of the airway tube 220. Other means and mechanisms for pairing and fastening the upper and lower tube sections together are likewise contemplated, including, but not limited to, use of elastic bands, and snapping the sections together. Importantly, though the airway tube 220 is depicted in FIGS. 12C and 13 including a flow resistance insert 280, it should be noted that, in some contemplated embodiments, the flow resistance insert can be removed or is not included at all.

Figure 14A:
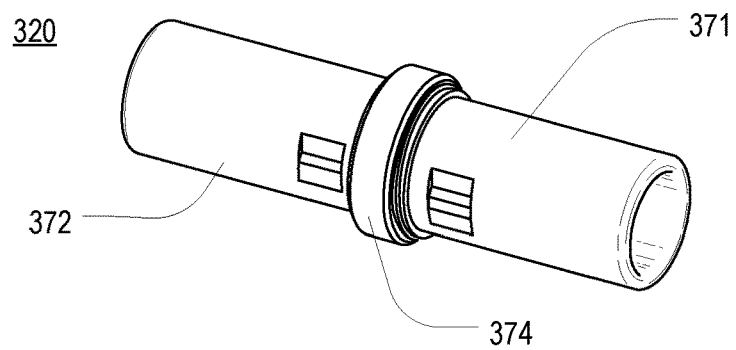
FIG. 14A is a perspective view of an alternative airway tube for a respiratory therapy instrument in accordance with one or more preferred embodiments of the present invention.
Figure 14B:
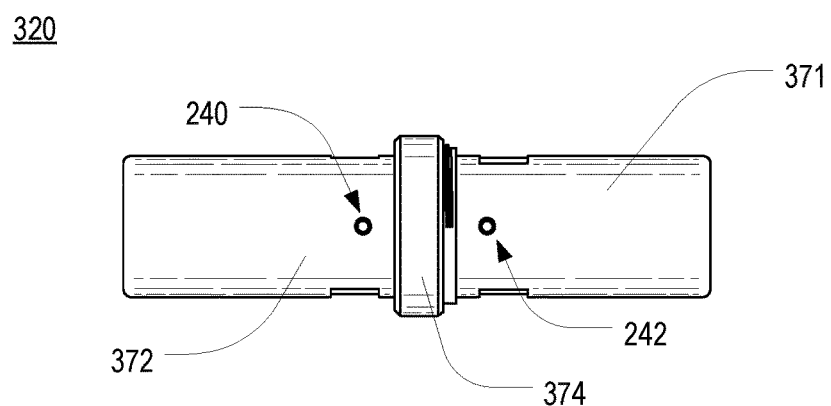
FIGS. 14B and 14C are bottom and end views, respectively, of the airway tube of FIG. 14A.
Figure 14C:
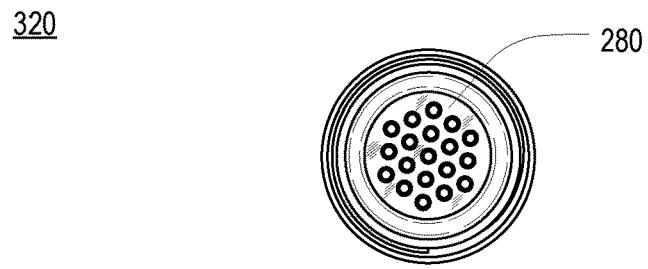
Figure 15:
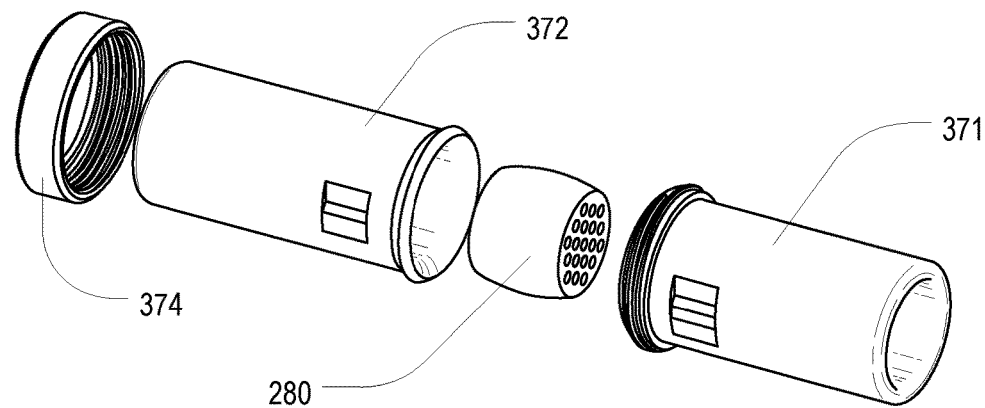
FIG. 15 is an exploded view of the airway tube of FIG. 14A, depicting a flow resistance insert contained within the airway tube.

In another contemplated embodiment, an airway tube 320 for use with the respiratory therapy instrument 210 can include laterally split components 371,372 that are paired to one another longitudinally. In this regard, FIG. 14A is a perspective view of an alternative airway tube 320 for a respiratory therapy instrument in accordance with one or more preferred embodiments of the present invention, and FIGS. 14B and 14C are bottom and end views, respectively, of the airway tube 320 of FIG. 14A. FIG. 15 is an exploded view of the airway tube 320 of FIG. 14A, depicting a flow resistance insert 280 contained within the airway tube 320. It is contemplated that the laterally split components 371, 372 can be permanently bonded to one another using adhesive or welds. It is further contemplated that the spit components 371,372 can be paired to one another in a non-permanent way so as to permit a user to be able to change or replace the flow resistance insert 280 held within an interior of the airway tube 320.

For example, it is contemplated that the split components 371,372 can be positioned adjacent one another to form a continuous length of tube with a nut 374 slid over the components 371,372 and tightened over inward-facing flanged ends of the split components in order to pair them together. The nut 374 is removable so that the components 371,372 can be separated so as to facilitate replacement of the flow resistance insert 280. It is further contemplated that the nut 374 is threaded. In this regard, the threaded nut 374 can be tightened against threads disposed along the flanged interior ends of the split components 371,372 to establish an airtight fit. Other means and mechanisms for pairing and fastening the split components together are likewise contemplated, including, but not limited to, use of elastic bands, and snapping the components together. Importantly, though the airway tube 320 is depicted in FIGS. 14C and 15 including a flow resistance insert 280, it should be noted that, in some contemplated embodiments, the flow resistance insert can be removed or is not included at all.

In yet another contemplated embodiment, the airway tube for use with the respiratory therapy instrument 210 is a unitary structure molded from a single cast. Such an embodiment is described above in connection with the respiratory therapy device adapter 10 depicted in FIGS. 1-3. It is contemplated that an airway tube constructed in this manner may be hollow or may contain a laminar flow section within the tube.

As discussed above, in some contemplated embodiments of the respiratory therapy device instrument 210, the airway tube 220,320 includes a flow resistance insert that allows the instrument to perform different functions. Flow resistance inserts, or pneumatic inserts, can be selected based on the specific task desired to be accomplished in order to facilitate a laminar flow through the airway tube 220,320. Different types of flow resistance inserts 280,290 are depicted in FIGS. 16A-17B. For example in FIGS. 16A and 16B, a Fleisch insert 280 is depicted. Use of a Fleisch insert 280 within the airway tube 220,320 can permit the respiratory therapy instrument 210 to operate in a manner similar to a clinical spirometer. In FIGS. 17A and 17B, a Lilly insert 290 is depicted. Other types of flow resistance inserts are likewise contemplated. For example, an insert containing a vibratory reed could be installed within the airway tube 220,320 to allow the respiratory therapy instrument 210 to operate in a manner similar to a PEP therapy device. It is contemplated that Fleisch and Lilly inserts 280,290, as depicted in FIGS. 16A-17B, are capable of installation in either of the airway tubes 220,320 depicted in FIGS. 12A and 14A. It is further contemplated that, depending on the selected task, a Fleisch insert 280 can be removed from the airway tube 280,290 and replaced with a Lilly insert 290, and vice versa.

Fleisch and Lilly inserts 280,290 provide laminar flow within the airway tube 220,320 through a known pneumatic resistance (R). This known resistance permits accurate measurement of airflow through the insert 280,290 and airflow tube 220,320, as will be described in greater detail below. Flow resistance inserts 280,290 are generally fitted into place before the airway tubes 220,320 are assembled. It is contemplated that a diameter of the flow resistance insert 280,290 can be larger than the diameter of the airway tube 220,320 in order to prevent the insert from moving within the tube, thereby helping to minimize or eliminate choking hazards. It is further contemplated that flow resistance inserts 280,290 may also be made of a compliant material that may be deformed upon fastening the tube components together in order to enhance the seal established between the insert and an inner surface of the airway tube 220,320. As will be described in greater detail below, a database of R values for a selection of therapy devices and pneumatic resistance standards is available either onboard the printed circuit board 216, on a computing device, or from a remote database. The user need only select the correct therapy device or flow resistance insert type from a computer screen, and firmware associated with the respiratory therapy instrument 210 can select the appropriate R value from the appropriate database.

In other contemplated embodiments, flow resistance inserts 280,290 can be used in conjunction with an attached respiratory therapy device, such as an IS or PEP therapy devices. In this regard, it should also be noted that additional resistance provided by the flow resistance insert 280,290 may not be desirable in some cases.

The circuit board 216 collects and digitizes pulmonary flow telemetry. The circuit board 216 also includes onboard sensing for detecting the orientation and movement of the respiratory therapy instrument 210. It is contemplated that the ability to sense motion can take the form of a motion processing unit (MPU) integrated into the circuit board 216. Orientation data may be used to track the position of the instrument 210 while held in the hand or in a mount. Movement detection can be used for establishing automated wake and sleep cycles for the instrument 210 as well as for detecting when to calibrate the pressure sensors 230,232 of the instrument 210 (as discussed in greater detail below).

In some contemplated embodiments, the MPU can be used for purposes of head tracking, which may be used as a positioning input for games. Furthermore, in some contemplated embodiments, the MPU can be used for purposes of step detection. Spirometry measurements using a clinical spirometer are oftentimes taken in connection with or following a period of user exercise. Inclusion of step detection capability in the respiratory therapy instrument 210, via the MPU, can facilitate measuring or quantifying a level of exertion immediately prior to a flow measurement. In use, a patient need only keep the respiratory therapy instrument 210 on his or her person during exercise so that the MPU can measure or quantify the user's level of exertion. It is contemplated that step detection measurements include, but are not limited to, counting steps and determination of the pace of user movement (i.e., running, jogging, or walking).

Figure 18:
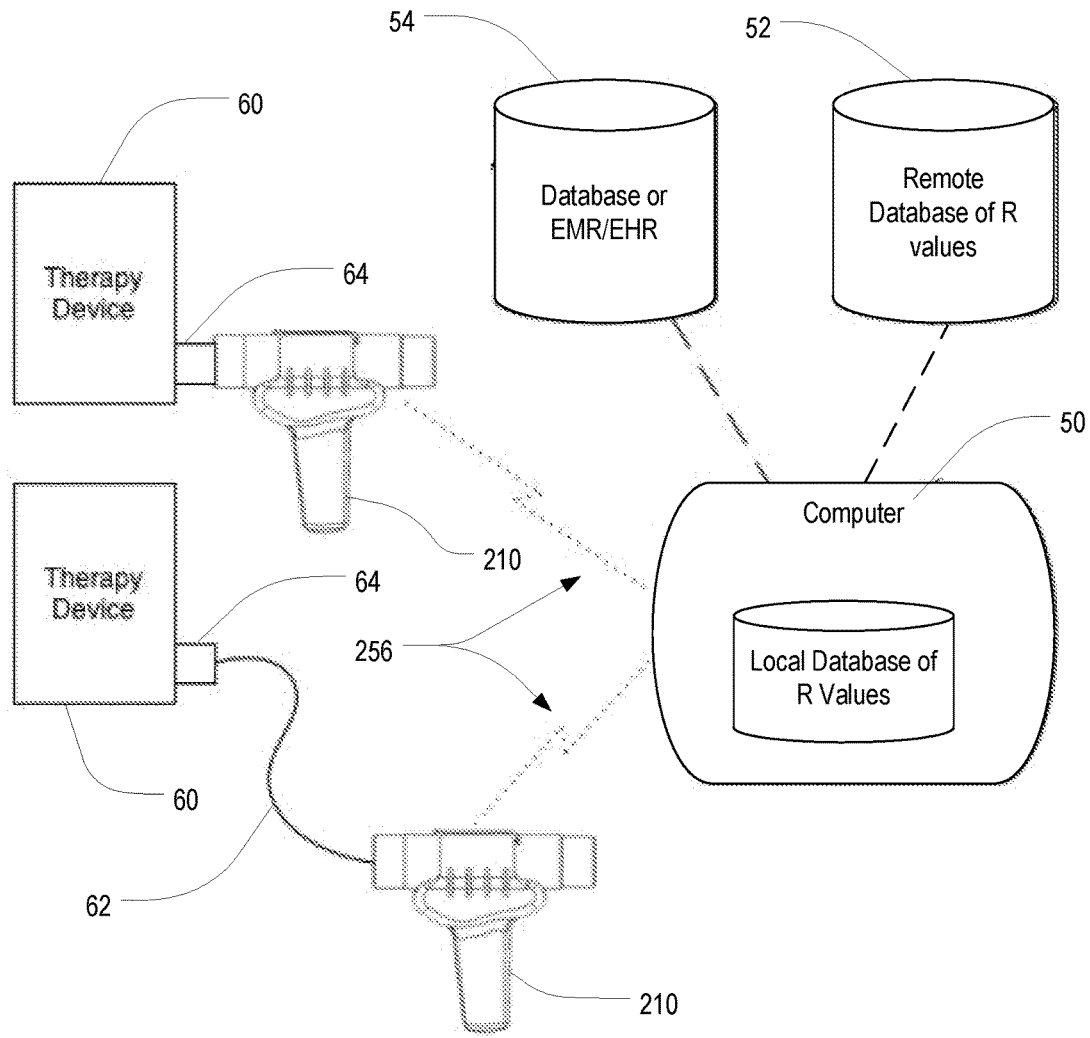
FIG. 18 is a schematic view of a system for transmitting wireless telemetry retrieved by the respiratory therapy instrument of FIG. 9 to a computing device.
Figure 19:
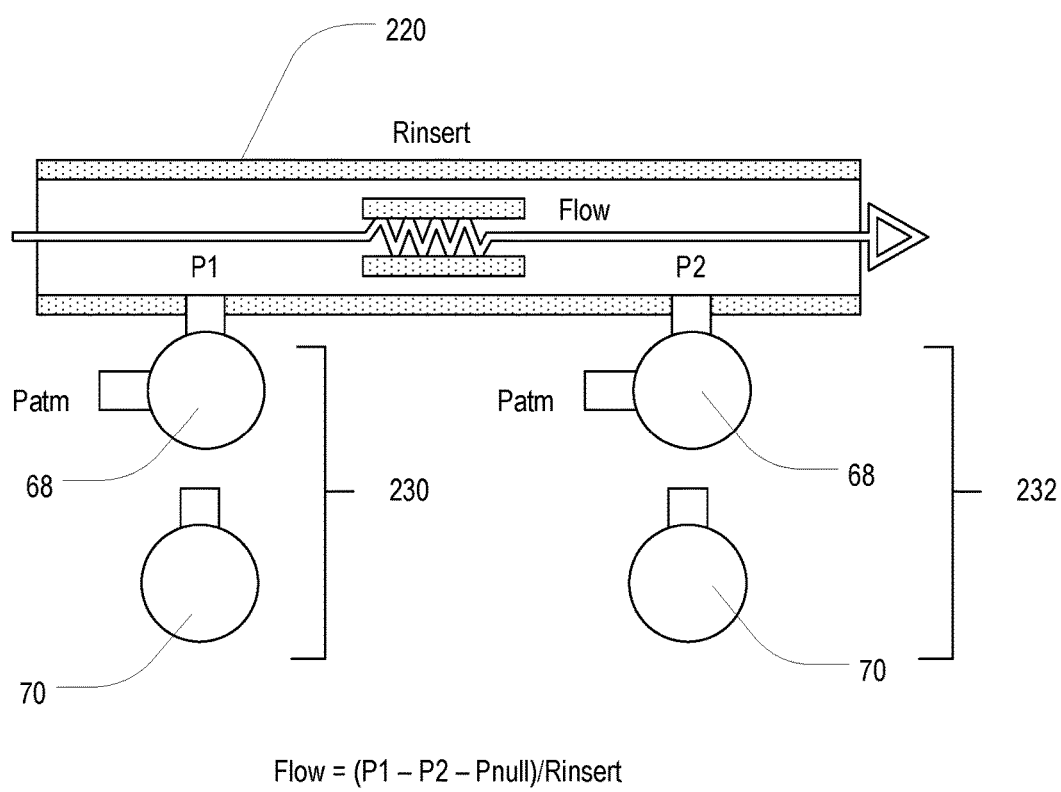
FIG. 19 is a schematic view of a system for measuring pressure and/or flow within the airway tube of the respiratory therapy instrument of FIG. 9.

FIG. 18 is a schematic view of a system for transmitting wireless telemetry retrieved by the respiratory therapy instrument of FIG. 9 to a computing device, and FIG. 19 is a schematic view of a system for measuring pressure and/or flow within the airway tube of the respiratory therapy instrument of FIG. 9. Importantly, the respiratory therapy instrument 210 is capable of use in multiple configurations. In one configuration, the respiratory therapy instrument 210 is used as an adapter for an existing respiratory therapy device, including IS and PEP therapy devices. When used as an adapter for an existing respiratory therapy device, the respiratory therapy instrument 210 can operate in a manner similar to that of the respiratory therapy device adapters 10,110 described in connection with FIGS. 1-8. In another configuration, the respiratory therapy instrument 210 can operate as a stand-alone respiratory therapy device, such as a clinical spirometer or as an IS or PEP therapy device.

When used as an adapter for an existing respiratory therapy device, it is contemplated that the respiratory therapy device instrument 210 can attach to a respiratory therapy device 60 either using a flexible hose 62 or directly to a port 64 of the therapy device 60, as depicted in FIG. 18. In adapter mode, flow sensing is accomplished using a pressure-drop method that is similar to a Fleisch or Lilly tube. The pressure drop across the therapy device 60 can be determined by subtracting the local atmospheric pressure ($P_{atm}$) at the outlet of the therapy device 60 from the pressure within the airway tube 220,320 ($P_{tube}$). Because flow resistance (R) of existing therapy devices is generally a known value (whether by laboratory testing or by testing with a patient using a known flow rate), the flow rate through the therapy device 60 and the airway tube 220,320 of the instrument 210 can be determined. In this manner, the therapy device itself can be used as a calibrated flow resistance. Flow resistance of the therapy device 60 is therefore able to be used as a standard across which a pressure differential (dP) is measured using differential/gauge 68 or absolute 70 pressure sensors. R values can be provided by a database of such values that correspond with a wide selection of therapy devices, as discussed in more detail below. This measurement technique and calculation methodology (dP=$P_{atm}$-$P_{tube}$) adds no additional pneumatic resistance into the patient's airway. As a result, when used in adapter mode, the respiratory therapy instrument 210 can measure flow through an existing respiratory therapy device 60, such as an IS or PEP therapy device, without any flow resistance inserts at all.

The ability to add flow resistance inserts 280,290 to the airway tube 220,320 can provide a variety of task-specific functionality to the instrument 210 and effectively permit the instrument to operate as a stand-alone respiratory therapy device (instead of operating as an adapter for an existing respiratory therapy device). With reference to FIGS. 12B, 14B and 19, when a flow resistance insert 280,290 is added to the airway tube 220,320, the pressure across the insert is known using gauge, or differential sensors 68 or absolute 70 sensors located at each port 240,242,340,342. With specific reference to FIG. 19, a first pressure determination (P1) is taken by the differential or absolute sensor 230 located upstream of the flow resistance insert, and a second pressure determination (P2) is taken by the differential or absolute sensor 232 located downstream of the flow resistance insert. Flow is determined by dividing the difference between pressures P1 and P2 by the pneumatic resistance of the flow resistance insert ($R_{insert}$). A nulling pressure ($P_{null}$) can be subtracted in order to account for any mismatch in atmospheric pressure readings of the two pressure sensors. R values can be provided by a database of such values that correspond with a wide selection of flow resistance inserts, as discussed in more detail below. Flow can thus be calculated as follows:

$$FLOW=(P1-P2-P_{null})/R_{insert}$$

The design of the pressure sensors 230,232 is such that additional resistance is not introduced into the airway. This can be advantageous when the instrument 210 is used in adapter mode with IS and PEP therapy devices, as significant resistance to the airway can be avoided when these devices 60 are attached. Furthermore, because sensing activity using the pressure sensors 230,232 does not require moving parts, the risk of choking hazards and other safety concerns can be mitigated or eliminated.

In contemplated embodiments, the pressure sensors 230, 232 of the instrument 210 are commercial absolute pressure sensors. One such commercial absolute pressure sensor available on the market is the MPL3115 absolute pressure sensor (designed as an altimeter), which is manufactured by Freescale Semiconductor Inc. of Austin, Tex., USA. When using an absolute pressure sensor, flow offset errors arising from changes in the local atmospheric pressure due to changing weather or altitude can be reduced or avoided entirely through continuous calibration of the absolute sensor.

In the case of an absolute pressure sensor, continuous calibration of the absolute pressure sensor whenever the instrument 210 is not in use (as detected by the MPU) can remove flow measurement errors arising from changes in barometric pressure due to weather patterns, elevation changes (such as by moving in an elevator) that might otherwise appear as a signal. Small flow bias can lead to large errors in calculation of total inhale volume, since inhale volume is a summation of instantaneous airway flow.

It is contemplated that flow bias for an absolute pressure sensor can be resolved by continuously (such as every 5 seconds) waking the respiratory therapy instrument 210 and checking to see if the instrument has been still since the last measurement (as detected by the MPU). Orientation of the instrument 210 can be assessed in the same manner. If the instrument 210 is still and not in an orientation implying that it is in use, then a series of local atmospheric measurements can be taken and a mean ($P_{cur\_atm\_mean}$) and standard deviation ($P_{cur\_atm\_std}$) can be calculated and stored. $P_{atm}$ is then set to the updated $P_{cur\_atm\_mean}$. Any changes in differential pressure (dP=$P_{atm}$−$P_{tube}$) that are smaller than some multiple of $P_{cur\_atm\_std}$ can be ignored. This process establishes a noise threshold that is dependent upon the local atmospheric conditions. In this way, as the instrument 210 is transported or as weather changes, the local atmosphere ($P_{atm}$ in FIG. 19) is continuously updated, thereby minimizing bias in the calculated pressure drop (dP) when the flow calculation is actually made.

A database of flow resistance (R) values 52 for a selection of therapy devices and/or flow resistance inserts is available either onboard the circuit board 216 or through a wireless connection to a computing device 50 or from a networked server. Whether used in adapter mode or in stand-alone mode, the user selects the correct therapy device and/or flow resistance insert from a computer screen, and firmware for the instrument 210 selects the appropriate R value from a database 52.

As depicted in FIG. 18, the circuit board 216 also includes a transmitter, such as a radio, for sending wireless telemetry 256 to a computing device 50. This telemetry 256 may include, among other things, pulmonary data, power level data, step count, or device orientation data. Data may also be stored locally on the instrument 210 for download to a database of electronic medical records (EMR) or electronic health records (EHR) 54 through the computing device 50. It is contemplated that the computing device 50 may be local to the user or remote. It is further contemplated that the computing device 50 can be any of a wide range of devices that include desktop computers, laptop computers, game consoles, mobile devices (such as a phone or tablet computer), and the like. The computing device 50 may be used for gaming, to provide the patient with training and real time feedback, to collect telemetry or other data, and to store R values for a variety of therapy devices and flow resistance inserts.

Utilizing the instrument 210 with games and gaming techniques provides a fast and easy way to keep patients interested in performing their exercises. Push alerts on the associated computing device remind patients when they need to perform an exercise. Taking advantage of attributes of the circuit board 216, including the MPU with head tracking and/or step detection, the instrument 210 can be utilized as a game controller, with the patient's breathing exercises being used to accomplish certain tasks within the game. It is contemplated that selected air flow targets (as established by the caregiver) can be indicated by LEDs or audio outputs on the instrument 210 itself as part of the game.

Within the game, real time feedback is used to guide each exercise. Training videos included in the game instruct the patient on how to setup and perform the exercise. Telemetry 256 from each exercise is saved on the computing device 50 and sent to a server 54 where it can be included in a patient's medical/health records. Processed data can inform caregivers whether the patent has been following the prescribed exercises as well as the quality (and trends) of the exercises. From this analysis, a caregiver can assess the efficacy of the prescribed treatment. It is further contemplated that collected data may be analyzed to detect coughing or wheezing that may be indicators for respiratory distress.

The instrument 210 helps to reduce the rates of pneumonia and other pulmonary complications in at-risk populations by either converting existing respiratory therapy devices to telehealth platforms that use gaming and alerts to incentivize patients to follow their prescribed therapy and collect data to report compliance and treatment efficacy back to caregivers or by operating as a stand-alone respiratory therapy device that provides a telehealth platform offering these same attributes. Whether used alone or as a complement to an existing respiratory therapy device, the instrument 210 provides a system that, among other things, facilitates patients being alerted by the computing device 50 when to perform their therapy based on a prescribed frequency or based on prior use data, incentivizes patients to use their therapy through gaming, trains patients in the proper use of their therapy devices using real-time feedback within the game, and reports back to the doctor or other caregiver compliance and pulmonary health trends. It is contemplated that the instrument 210 is usable both as a preventative and as a treatment for pulmonary complications in chronic (long term such as nursing home) and acute (short-term such as post-operative) populations.

Implementation of the instrument 210 in adapter mode with existing respiratory therapy devices, including IS and PEP therapy devices, improves these devices by, among other things, automating patient training and coaching, automating data reporting; incentivizing use of the therapy device, and/or facilitating the collection of total inhale/exhale volume for therapy devices that do not have such a measure.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A respiratory therapy system for establishing a telehealth platform for pulmonary care comprising:
   a respiratory therapy adapter including,
      a housing,
      an airway tube removably secured to the housing for accommodating a flow of air, a first absolute pressure sensor in communication with an interior of the airway tube at a first location, a second absolute pressure sensor in communication with the interior of the airway tube at a second location, and a circuit board retained within the housing, the circuit board including a transmitter for transmitting data to a computing device; and a separate respiratory therapy device including a first flow resistance insert disposed in an airflow pathway;

wherein the airway tube of the respiratory therapy adapter is in fluid communication with a port of the airflow pathway of the separate respiratory therapy device;

wherein the circuit board provides access, via the computing device, to a database of resistance values corresponding with a plurality of flow resistance inserts, including the first flow resistance insert, to facilitate identification of a first flow resistance value associated with the first flow resistance insert of the separate respiratory therapy device;

wherein the first flow resistance value is usable with pressure data detected at one or both of the first and second absolute pressure sensors to ascertain a flow measurement through the separate respiratory therapy device;

wherein the housing is a multi-component housing; and wherein the multi-component housing includes first and second tubular portions secured to one another longitudinally with a threaded nut.

2. The respiratory therapy system of claim 1, wherein the separate respiratory therapy device is an incentive spirometry device.

3. The respiratory therapy system of claim 1, wherein the circuit board includes the database of resistance values.

4. The respiratory therapy system of claim 1, wherein the computing device includes the database of resistance values.

5. The respiratory therapy system of claim 1, wherein the computing device includes a tablet computer.

6. The respiratory therapy system of claim 1, wherein the computing device includes a mobile telephone.

7. The respiratory therapy system of claim 1, wherein at least one of the pressure data and the flow measurement is utilized in game play for an incentivization game operated on the computing device.

8. A respiratory therapy system for establishing a telehealth platform for pulmonary care comprising:
a respiratory therapy adapter including,
a housing,
an airway tube removably secured to the housing for accommodating a flow of air, a first absolute pressure sensor in communication with an interior of the airway tube at a first location, a second absolute pressure sensor in communication with the interior of the airway tube at a second location, and a circuit board retained within the housing, the circuit board including a transmitter for transmitting data to a computing device; and a separate respiratory therapy device including a first flow resistance insert disposed in an airflow pathway;

wherein the airway tube of the respiratory therapy adapter is in fluid communication with a port of the airflow pathway of the separate respiratory therapy device;

wherein the circuit board provides access, via the computing device, to a database of resistance values corresponding with a plurality of flow resistance inserts, including the first flow resistance insert, to facilitate identification of a first flow resistance value associated with the first flow resistance insert of the separate respiratory therapy device;

wherein the first flow resistance value is usable with pressure data detected at one or both of the first and second absolute pressure sensors to ascertain a flow measurement through the separate respiratory therapy device;

wherein the housing is a multi-component housing; and wherein the multi-component housing includes upper and lower sections paired together with one or more tapered collars.

9. The respiratory therapy system of claim 8, wherein the separate respiratory therapy device is an incentive spirometry device.

10. The respiratory therapy system of claim 8, wherein the circuit board includes the database of resistance values.

11. The respiratory therapy system of claim 8, wherein the computing device includes the database of resistance values.

12. The respiratory therapy system of claim 8, wherein the computing device includes a tablet computer.

13. The respiratory therapy system of claim 8, wherein the computing device includes a mobile telephone.

14. The respiratory therapy system of claim 8, wherein at least one of the pressure data and the flow measurement is utilized in game play for an incentivization game operated on the computing device.

* * * * *